(12) United States Patent
Rigatti et al.

(10) Patent No.: US 10,006,081 B2
(45) Date of Patent: *Jun. 26, 2018

(54) END MODIFICATION TO PREVENT OVER-REPRESENTATION OF FRAGMENTS

(71) Applicant: Illumina Cambridge Limited, Nr Saffron Walden (GB)

(72) Inventors: Roberto Rigatti, Nr Saffron Walden (GB); Niall Anthony Gormley, Nr Saffron Walden (GB); Helen Rachel Bignell, Cambridge (GB)

(73) Assignee: ILLUMINA CAMBRIDGE LIMITED, Essex (GB)

( * ) Notice: Subject to any disclaimer, the term of this patent is extended or adjusted under 35 U.S.C. 154(b) by 279 days.

This patent is subject to a terminal disclaimer.

(21) Appl. No.: 14/666,839

(22) Filed: Mar. 24, 2015

(65) Prior Publication Data

US 2015/0197789 A1 Jul. 16, 2015

Related U.S. Application Data

(63) Continuation of application No. 12/223,761, filed as application No. PCT/GB2007/000427 on Feb. 7, 2007, now Pat. No. 9,012,184.

(60) Provisional application No. 60/771,358, filed on Feb. 8, 2006.

(51) Int. Cl.
  *C12Q 1/68* (2018.01)
  *C12N 15/10* (2006.01)
  *C12Q 1/6806* (2018.01)
  *C12Q 1/6855* (2018.01)

(52) U.S. Cl.
  CPC ....... *C12Q 1/6806* (2013.01); *C12N 15/1093* (2013.01); *C12Q 1/6855* (2013.01)

(58) Field of Classification Search
  None
  See application file for complete search history.

(56) References Cited

U.S. PATENT DOCUMENTS

| | | |
|---|---|---|
| 5,817,797 A | 10/1998 | Mitchell et al. |
| 5,876,932 A | 3/1999 | Fischer |
| 6,413,518 B1 | 7/2002 | Koelle et al. |
| 7,741,463 B2 | 6/2010 | Gormley |
| 9,012,184 B2 * | 4/2015 | Rigatti ............... C12N 15/1093 435/91.2 |
| 2003/0049657 A1 | 3/2003 | Cherry |
| 2003/0143599 A1 | 7/2003 | Makarov et al. |
| 2004/0185484 A1 * | 9/2004 | Costa ................ B01L 3/502707 506/14 |
| 2004/0209299 A1 | 10/2004 | Pinter et al. |
| 2006/0024681 A1 | 2/2006 | Smith et al. |
| 2006/0046251 A1 * | 3/2006 | Sampson ............. C12Q 1/6834 435/6.18 |
| 2007/0172839 A1 * | 7/2007 | Smith ................. C12Q 1/6855 435/6.12 |
| 2008/0194414 A1 * | 8/2008 | Albert ................. C12Q 1/6834 506/1 |
| 2009/0233291 A1 | 9/2009 | Chen et al. |

OTHER PUBLICATIONS

Sterky F, Holmberg A, Alexandersson G, Lundeberg J, Uhlén M. Direct sequencing of bacterial artificial chromosomes (BACs) and prokaryotic genomes by biotin-capture PCR. J Biotechnol. Feb. 5, 1998; 60(1-2):119-29.*

* cited by examiner

*Primary Examiner* — Angela M. Bertagna
*Assistant Examiner* — Olayinka A Oyeyemi
(74) *Attorney, Agent, or Firm* — Illumina, Inc.

(57) ABSTRACT

The invention relates to a method of preparing a 5' and 3' modified library of template polynucleotides and also the use of the 5' and 3' modified library of templates in methods of solid-phase nucleic acid amplification. In particular, the invention relates to a method of preparing a 5' and 3' modified library of template polynucleotides which have common sequences at their 5' ends and at their 3' ends, wherein over-representation of "end" sequences of the primary polynucleotide molecules from when the 5' and 3' modified library is generated is greatly reduced or prevented.

13 Claims, No Drawings

SEQUENCE LISTING

```
<160> NUMBER OF SEQ ID NOS: 38

<210> SEQ ID NO 1
<211> LENGTH: 20
<212> TYPE: DNA
<213> ORGANISM: Artificial
<220> FEATURE:
<223> OTHER INFORMATION: Synthetic Primer

<400> SEQUENCE: 1
cgaggaactc agcactcatc                                               20

<210> SEQ ID NO 2
<211> LENGTH: 20
<212> TYPE: DNA
<213> ORGANISM: Artificial
<220> FEATURE:
<223> OTHER INFORMATION: Synthetic Primer

<400> SEQUENCE: 2
atgccgagga agaagccatt                                               20

<210> SEQ ID NO 3
<211> LENGTH: 24
<212> TYPE: DNA
<213> ORGANISM: Artificial
<220> FEATURE:
<223> OTHER INFORMATION: Synthetic Primer
<220> FEATURE:
<221> NAME/KEY: misc_feature
<222> LOCATION: (4)..(4)
<223> OTHER INFORMATION: 'n' is an abasic nucleotide

<400> SEQUENCE: 3
tttntggaac agccgctctc acct                                          24

<210> SEQ ID NO 4
<211> LENGTH: 24
<212> TYPE: DNA
<213> ORGANISM: Artificial
<220> FEATURE:
<223> OTHER INFORMATION: Synthetic Primer
<220> FEATURE:
<221> NAME/KEY: misc_feature
<222> LOCATION: (4)..(4)
<223> OTHER INFORMATION: 'n' is an abasic nucleotide

<400> SEQUENCE: 4
cccntcctgg agggaagtga ctat                                          24

<210> SEQ ID NO 5
<211> LENGTH: 10141
<212> TYPE: DNA
<213> ORGANISM: Homo sapiens

<400> SEQUENCE: 5
cgaggaactc agcactcatc ctcacccagc agggcataag ggtttcggcc agccaggctg    60
gaccctggag ccgaggttgg ggtctcctca tcccttctc cctcctcatc cgcatcccgg    120
```

```
tcctcctctc cctcctcctc acaggagctg ctcagctctt cctcttcctc ctcctcctcg    180
tcacctgctg gccccaccct gccctgcaaa accaccagct ccgtggtctc tggatgggac    240
tcccaggtgc ctggggaacc aaaacaagaa aaaatggag gagagttttg agcaagaact    300
aaagccaagg aaagatgggg aagaggcaaa gactaggaat aacaataatc tttagagctg    360
ctggcattca ttcattcatc cattcattca acttcctatg tgcagattgc tgaacagaac    420
ctttgtgcac atcaacttca atctttacaa tcactatgct aagggtcaat tattaccctc    480
agtttgcaga tcaggaaaat atcacagatg ttaagtaaca gagctagcca acaggtacag    540
aatccaggtt tgaccctctc tctggccaca aagcccacac ccttttacct acgctatagc    600 aggggctgg ggaagaatat ctgggctctg acctttctgt tcactgtagc ctggggatg    660 aaaacacagg ctgaggcggc cgtccactgc cagccgcaag agactgttgg ctgctctgta    720
cacatcattc cgagccgcct tggctgtctt gtaaccacgt ttctctgccc aggctggagg    780
aagaaaagaa taatgaaag ggaaagcatt aaccaggtac cagttatact cccactccca    840
taacacagtc cttccagttt tccccaaaac attccaggcc agagatctta ctggctatgc    900
aacaaaaatc taggggtgag tggacagcag cttcatcaat ggcagaatct ctgaggagag    960 gaaggagac agggaagggt aaaaggcgag gcaggtaagg aagagcagct gaaaccaggt   1020
ggggcgaagc caggcacatg gaactcacct tcacagatgt cccaggcaca ccaggggtgt   1080
tccgctgagg ggtcctcagc ctctgggtgg cgcaggtgga gcagggcctg cacgggaatt   1140
cgggaggcca ggtagcccac agcagtgtag ggctcctgga tctgggcgat agggtagatc   1200
cccgccagaa cctgagggaa atgagcactc agtactttcc tcaatgtccc accttctctc   1260
tttcccttac ccaccctccc cgtcatacct gcaactgcct aggcagaaga gatgggaaga   1320
tgaggcctgg gcagtcacag agcttcacag aggggtaag aaagtaggtc tgaaagtatc   1380
gggtatggcc cggggttctg gagacactca cgactttccg ccccaccagc ccattgatca   1440
gcgaggactt tcccacatta gggaaacctg aggaaggcaa ggaaaattaa cgtttaacag   1500
gtttctactc tgtgatggga cttggtgcta tacctatagg taaaaggggga actaaggctc   1560 agaaattaag gaaatggtat tgcagaatac aaatcacgct ctgggctgcc agggttaaat   1620 cctggcccctt ccacttacca gctttgtgat gtcagggcaa ctaactttct gagcctctgt   1680
ttcttcattt tacagtgtgg acacctccct acctcagggt ggtcaggatt aaatgagata   1740
accaatacaa cttgtgtggg tcagtgcctg cagtacagta agtacccagt accagtgatc   1800
cacatctcat aattactatg acttggcctg gcacagtggc tcacgcttgt aatcccagcg   1860
tgattacttt gggaggccaa ggcgggtgga tcacctgagg tcaggacttc aagaccagcc   1920
tggccaacat ggtgaaaccc catctctact aaaaatacaa aaattagctg ggcgtggtgg   1980
tgggcgcctg taattgcagc tacttgggag gctgaggcag gagaaccact tgaacccagg   2040
aggcggaggt tgcagtgagc tgagattgca ccattgcact ccagcctggg caataagagg   2100
gaaactccat ctcaaaaaat aataataata attacgatga cttgtccaag gagaaaactg   2160
gaagccttgg ggctcactgc cactctgctc actcaccacc accagttttt gtgtttctgg   2220
ctgacttcag tgccttcatc tcccttccac agagcatctc cttttacccca cctcagctgc   2280 ccactcccat ggtaatacct gcatcttgtc acttcacagc tccaaagcct caattccaag   2340
cacccctctc tgccctgaca actcatcttt ccagctcact tactctggtt actccatgcc   2400
agtaagtctt tgaccctga ccttaacaca gtaacactat gcaatacca actcgtgtcc   2460
```

```
tcaatttcct tcttacttga ctcagatttc atgatccagc tcctcagcca gggccgttca    2520
cagacctgga actccctggt cccacttctc ccctctatct tactcacctg gcaaaatccc    2580
aaccctgtaa aatccagctc tgcccattca gcactgctcc tgggcagctg actgtggcta    2640
agaaaagatg taccactgtg ctcactcttt acaacacatg caagtatcta ggaggaaggg    2700
agggaaggag ggagaaaaaa gttctccttt gacgaccacc accagaccta gttctctgtc    2760
cgctttgcag gaaaactcct taaaagactt acctactttt ttcaccattt cttcctgcta    2820
tcttctttgt aactgtaaac tacaacatac aaaaaaatgc acagaacata catgtgcagc    2880
ctgatgaacc ccataccacc caatgtgtga caacatgttc catctgtcct tgttttttt    2940
tgttttgtt tttgagacag agtctcactc cctcacccgg gctggagtgc agtggtgcga    3000
tgttggctca ctacaacctc atcctcccag gttcaagcga ttctcgtgcc tcaacctcct    3060
gagtagctga gaccacaggc gtgcggctcc acacctggct aacttttgt attttagta    3120
gagatagggt tttgccatgt tggccaggct ggtctcaaac tcctgacctc aagtaatgcg    3180
cctgcctcag cctcccaaag tgctaggatt acagggatga gccaccatac cggccgccac    3240
tcatccttct tgatcataat cctctccctc tatacatgca agcttatcc ttttaaggaa    3300
atcaactcct tacatttctc tttagtttat gacctgtgta tctctcaaca atgcagctta    3360
attttgcagc tttcaaactt gatagaactg aaattgtgca gtatggatgc tattgggtca    3420
gactcttttc acacaatgtt atgtgaagtt gttgcacctt ctctcatggg cctactccag    3480
tttggctttc tccaccccac tgaaaccacg gatcttcaca ttgccaagcc tgctgagcag    3540
ctctctgttc tctcatttgg cctgtcagca acagttgaca cagctgattc ctcctttcct    3600
cttcaaacac cttcttcatt tgacttctgg gacgctccct tggttttcct ccttctcact    3660
gtcctttgcc caactaaatg ctggcttgtc ctaaggctca gtccttgacc tcctcttctc    3720
caactatttc cttctctcc tacatctcat ccaattccat ggcttttt ttttttttt    3780
tgacgaagtc ttgctctgtc acccaggctg gagtgcagtg gtatgatctt ggctcaccgt    3840
aacctccgcc tccaggattc aagcaattct cctgcctcac cctcctgagt atctgggact    3900
acaggcacgc accaccacac acggctaatt ttctgtattt tttggtagag acagggtttc    3960
accatgttgg ccaggctggt ctcaaactcc tggcctcaag tgatccacct gcctcagcct    4020
cccaaagggc tgggattata ggcatgagcc actgtgccca gcctaatcct gtggctttaa    4080
ataccactta tatccatcaa tggttcccca aatttaaatc tttcccaaat tcaaatttcc    4140
gtcctcttct ctcccctaag ctgctgacta cttaccact gccattcaa catctccact    4200
agggatattt aaaaagaatc tgaaatttca tttctgattc ccctctcctc cccaaagcct    4260
tcaaatctgc ttctccccca gtcttccat ctcagtattt ccagttgctc aagacaaaaa    4320
cctggaagtc cttctttatc ctcacttcc ttcacgtgcc aactgcaagc catcagcgat    4380
ctcattttct ctaccttcaa aatatatcat gcttccggcc ctgtctcacc acctccagct    4440
ccagcatcct actctaagca actcttattt ctctcctaga ttactgaaat agcctcaact    4500
gctctctctg ctcccttct tgcccacccc ccatcattta ttctctactc aggaggtaaa    4560
cttataagaa acaaaatcag atcctatcat tccctgttc aaaacctacc cttggcttct    4620
catgagactt ggaataaaat ccaaaatggc tgtcacagcc tcagggctct acatgatgtg    4680
ggccctggtg atcttgctga cctcatcccc agtactttat cctggctccc atactccaat    4740
cccctgggca ctcttgctgg tcctagaatc tccaagccca ttccctcctc aagaccctt    4800
ccccacagtt ctgaatggct cacttcatct catcatccag ttctctcctc agggaggttt    4860
```

```
tccctgagca cctctcctct cagtcactct ctatccccttt tcattgctttt attgccttca   4920 ctgcccctac atgatttcgg atcacaaaat ctatttactc acaagaaaat aagctccatg   4980
aatctacaga ccttttttgcc atttccacag cagtatgtcc catccctaga atatctggca   5040
cctggttaag tgttcagtac atatttgttg aatgggtaaa tgaatgagag ctggagggaa   5100
atccaaactc aggggtgcct gtgccacagc aaacactctc cctctcacac cacctggaat   5160
agagatcagc tagagcagag gctgctaaga gagggaacag aggctccttg tgacagggag   5220
actaggatca gaagtcaggg aagggacagc cgggtgaaat gactggaaag aggagcaatc   5280
actcagcagt aaggcaggtt cttccaaaga caaaaaggac acagagataa gtcagggcac   5340
ttccaaggaa cccaactacc tactccacac tcccaaattt attctgggtt gggccctttt   5400
tggttccaat atcacctcgg ataccataac ttgtccaagg tctcttctta cctctcccac   5460
cctaaatgaa gacgggccct gggtcctaat catacattcc tttttcctcc actgtgagct   5520
gagacaaagc ccttaagagg agattctcct tggcaacaaa cttaaagggt taaaacctag   5580
aagaatacta attcttgctg agctcctact atgatttgat aatcactgta ctacagacta   5640
attactacaa ttcaaatggt ttatataaac cacttaaaac agtgcctgtt acatagtaag   5700
caccatataa atactgagtt ttaacaataa taattgttat tattgttatc actatttgtc   5760
aggcattctt acactctctt aacactattc ccatcattcc tcacatccat tcttttttt   5820 taaagacagg gtctctatca gccaggctgg agtgcagtgg cacaatcata gctcactgca   5880
gccttgaact cttgggctca agtgatcctc ctgcctcagc ctctgaagta gcagagacta   5940
caggcacata ccaccacact tggctagttt tctttatctt ttgtaaagat ggggtttcac   6000
tatgttgccc acactagtct tgagctcctg gtctcaagca atcctcccac ctcagcctcc   6060
caaagcgctg ggactatata ggcatgagcc ctcacacatg gccgtcatcc attcttttac   6120
tcaggtatca atgtccttat ttttaaaatc aaagtaacta agactcagag tagcaaaatc   6180
acttactcaa gacctcacag ctgagaagag gtggaattta actcaggctg tcatgatcct   6240
tccactgcag cagacgcctc ttctgccttg cccaccgcca ctggcagaga tcacccctca   6300
gacaccctgg ggcctaatga gacctgatcg ccctctctct tctccgaata tgaaaactct   6360
gtacctcctt ggaggccacc acgcacaagc tgccacttcc ttaccacac agccgatggt   6420 caccacccca tccttgtagc gctcttgggt tgggccagtt ggctccattg ctgaatcagt   6480
ctgctgctcc accaggactg ctgggccatc ctcctcttcc tcctcctccc cagagccatt   6540
accccaggtg gccccagcca catcccgagc aatcttctcc cgccagctgc tcaagtccac   6600
tgctcaaaga aggagaagat taaagaggtt ctccccaggg ctgctgtgca tgatggcaca   6660
tactgtgccc tgcacagatt atgtaactgg caccctctgg agttgtacag tgccaaccta   6720
aataagagca ggtcagagaa tctcccaaaa gtcatttgac cctaccctcc ctggaatcac   6780
gcacgtttct ctgagcttct gaaaagtact gggaaggcta aagcagcaa gccactgagg   6840 ctcctgacta cctgctgcct ctcgtcccac caagtcagtc tgctccttat tctgtccctt   6900
cccctggcct cttgcacata tccaccatag aggggttggc ttcaggaaag gtgagcaaaa   6960
tgattctgca tctttggtct cccccatgtc ctcctacagc cctcctctaa gggccacata   7020 cctttccccca cagtgatggc ttcacaggct ctcagcaact gctctggccc cagggcccga   7080
gtccatcctc tcccccgcct ccgactcttc ttcaagactg agatcagagg gcacaaaagg   7140
atgggcacac gggcttaggc ctctcatctc tcccaccacc cttaggccca agaccaggtg   7200
```

```
ccccttgtc aataagcctc tctgttctcc cctttgtccc ctgccaactc acctctccca    7260
agttgccctc tctcattgcc cactcaccac tactaggatc ctgtggggtg cgggggtccc    7320
gaggaaaaga ggtgaaaagg acgacgtgga gctggggata gtgttgatgg aaataatgct    7380
tccaggcaac cacaagagct ggcggggcca gatccacctt gttcaaaacc agcaccaggg    7440
ccagtccaag ttctccagtc acatactcat aaagtgctgg cgggaaattc acaacctagg    7500
acagagttga taagaggatg gagcagtgaa agtcaaccca gagttctctg cctccagctc    7560
cccactcagc aggtgtagct cagagacaag gccctggtgg tagcagactc tgggctaaaa    7620
actataaacc agacaaactg aaaaacaaag acaaaacagg ggttagtaat acttctgagt    7680
ctcagagggc ttcctatagg tcatgattag agatggaaat gaacccaaaa caagacaagg    7740
aaacagcatc acttagcaca ctgaggtaaa ggctgggatc ggaaacaggg atggggggtta   7800
gggtagaaat tagtctgctt ttttgtgtgt gcacaactat gtaagtgtgt acacgtgcat    7860
atatgcatgc atgcaagtac gtgcacatgt gtgcatgttt gtgtgttaat gtgactgtga    7920
acatgtgtgc aaacatgcct gtgtatattg atgtgcacat gatgtacgtg tgagtatgtg    7980
tgtgtacata ttattaagga cctccaacct aaatggtcct cacagacctc cctttctccc    8040
actggaggac aagagtgaag ttgcagagct aggattcaca cagggcagtc cagcagcagt    8100
ctacagcctt aactactact ctagcattcc aggtgggttc tgtagcaact gatgtggcag    8160
tgctagagaa atgagataag gaagaaaggg catctttggg ctgggcagga ggaagtcccc    8220
agctgcattc atagaatccc tggagctcca cacttggat tttctattgg tctgtgatga     8280
gctaaaggac aggacatggc tgttttgaag agaagagtga gctggccaag ggaggaatga    8340
caggctataa gagaataaaa aactgagttc ctaactgcgg acatcagcac taggtagaga    8400
ttagaaagac aggaagatag ataactctct gtctcccaac tcttgcctct gaccttttgcc  8460
cctgaaaaac ctttctccct cctccttgcc caccctattc cctagtactc actggatgtc    8520
ggatatcagt gataagcagg acgatgtcag acatctctaa cacccgccac agctgcctcc    8580
atgtctaaaa agacaggatc aggaagagaa actgaaaaca gagtccctct ccagcctgat    8640
cccaaaccaa tttgaccata ggtcactatg ccccactcct gtccctagag tacactgtca    8700
cctccagatt gtgctcaaag tagctgagtt tctcagagga gtaagcccca tgaatcttcc    8760
caagatagtc ttggaagctc cgttcctctt ggctcattag ttgctccttg acatctcat    8820
agctccaagg aggacgtcga ggaaagtcca gaactgggaa ttcaggaaaa agtccaagtg    8880
tgaggaaatc ttcaggattc aagagtacat cccagacccc tccttcctca cagtcggctt    8940
ttacctttcc aaaactcctt cccagcccaa tgcctgtctt gctctcactc acctgagcca    9000
ggctgataca cctcccggat gtccagctcc acaactcag cactgaccgg ctgtagaact     9060
tgctcccggg ctgctctctt tctcctctct acctcctccc tgctgtctct ctcaaaatgc    9120
agtcggtatc taaggaaca gggaccgaga catccgagc aatcctgtgg ccacaaactc      9180
ctatttctc ccctcttgta caatcaactt cgcaaaccat tctctccaga gtcgttcaag     9240
tctcctctct caagtcagac ttcccccaag tccttctttc aggcaatact cagccttctc    9300
cttctaaaag cccaactctc tccagcccct ctggaaagga agactgtggc ccgctgtggg    9360
gagccgagtg gctagcggag aactgtggca tcccaggccc accgtcttca ccagtagcag    9420
cccgctttcc cccaaagctc tgacttccgg gtaggcggga aagccgggac cagcgccccc    9480
tcccacctc accgatttgg gtcgtagcct cgtggaccca gccctgaga aggctgctgg      9540
ttaagcctgc ggatatgatg ggtcacagac tccccgtccg aggtgtcggt ctgttcctct    9600
```

| | | | | |
|---|---|---|---|---|
| cgccgctccc | ggctcccgct | gcggctgttg | gaactggagc gcagcccatc ttgaagccct | 9660 |
| gcggggaggg | gccggtgacg | ccagtgctgg | ccagctctca ggggcataa gaccctctcc | 9720 |
| cccatcggcc | tgactccctt | tcatcccact | caacttcttc cgatgttcag tcctcccaga | 9780 |
| caccctattt | gggaccctcc | cggatgtgcg | tgggggagt cactccttca gggagcagtg | 9840 |
| gggacggcgc | ccgtgctag | ctggagggat | tcccctcccc caactctcca tccttcccca | 9900 |
| cccttccag | atgtagggg | ggtgggat | ccctccgcg ataggccgcg agggttgacg | 9960 |
| cggtcccacg | accccctccc | acgatcccca | gaggtgcagc gggcacaccc ctccttccag | 10020 |
| atgtgcggaa | gcccgagccc | cgccccctcc | tcccgctccc gcactgacct ctcttccgct | 10080 |
| cccgtttgtc | ctgcaactgc | ttcttcttct | gcttcacgct gaatggcttc ttcctcggca | 10140 |
| t | | | | 10141 |

<210> SEQ ID NO 6
<211> LENGTH: 10486
<212> TYPE: DNA
<213> ORGANISM: Homo sapiens

<400> SEQUENCE: 6

| | | | | |
|---|---|---|---|---|
| tggaacagcc | gctctcacct | cagttcatct | ggggaagggg ctacaaagca acaatctttt | 60 |
| attcacaatt | ggggtggcag | aggggagata | cccccaggtc agtccaaaag caaagatact | 120 |
| gggagggaag | atggcgctgg | gcgaggaact | cagcactcat cctcacccag cagggcataa | 180 |
| gggtttcggc | cagccaggct | ggaccctgga | gccgaggttg gggtctcctc atccccttct | 240 |
| ccctcctcat | ccgcatcccg | gtcctcctct | ccctcctcct cacaggagct gctcagctct | 300 |
| tcctcttcct | cctcctcctc | gtcacctgct | ggccccaccc tgccctgcaa accaccagc | 360 |
| tccgtggtct | ctggatggga | ctcccaggtg | cctggggaac caaaacaaga aaaaaatgga | 420 |
| ggagagtttt | gagcaagaac | taaagccaag | gaaagatggg gaagaggcaa agactaggaa | 480 |
| taacaataat | ctttagagct | gctggcattc | attcattcat ccattcattc aacttcctat | 540 |
| gtgcagattg | ctgaacagaa | cctttgtgca | catcaacttc aatctttaca atcactatgc | 600 |
| taagggtcaa | ttattaccct | cagtttgcag | atcaggaaaa tatcacagat gttaagtaac | 660 |
| agagctagcc | aacaggtaca | gaatccaggt | ttgaccctct ctctggccac aaagcccaca | 720 |
| ccctttttacc | tacgctatag | caggggggctg | gggaagaata tctgggctct gacctttctg | 780 |
| ttcactgtag | cctgggggat | gaaaacacag | gctgaggcgg ccgtccactg ccagccgcaa | 840 |
| gagactgttg | gctgctctgt | acacatcatt | ccgagccgcc ttggctgtct tgtaaccacg | 900 |
| tttctctgcc | caggctggag | gaagaaaaga | ataatggaaa gggaaagcat taaccaggta | 960 |
| ccagttatac | tcccactccc | ataacacagt | ccttccagtt ttccccaaaa cattccaggc | 1020 |
| cagagatctt | actggctatg | caacaaaaat | ctaggggtga gtggacagca gcttcatcaa | 1080 |
| tggcagaatc | tctgaggaga | ggaaaggaga | caggaagggg taaaaggcga ggcaggtaag | 1140 |
| gaagagcagc | tgaaaccagg | tggggcgaag | ccaggcacat ggaactcacc ttcacagatg | 1200 |
| tcccaggcac | accaggggtg | ttccgctgag | gggtcctcag cctctgggtg gcgcaggtgg | 1260 |
| agcagggcct | gcacgggaat | tcggaggcc | aggtagccca cagcagtgta gggctcctgg | 1320 |
| atctgggcga | tagggtagat | ccccgccaga | acctgaggga aatgagcact cagtactttc | 1380 |
| ctcaatgtcc | cacctctct | cttttcccttta | cccaccctcc ccgtcatacc tgcaactgcc | 1440 |
| taggcagaag | agatgggaag | atgaggcctg | ggcagtcaca gagcttcaca gaggggtaa | 1500 |

```
gaaagtaggt ctgaaagtat cgggtatggc ccggggttct ggagacactc acgactttcc   1560
gccccaccag cccattgatc agcgaggact ttcccacatt agggaaacct gaggaaggca   1620
aggaaaatta acgtttaaca ggtttctact ctgtgatggg acttggtgct atacctatag   1680
gtaaaagggg aactaaggct cagaaattaa ggaaatggta ttgcagaata caaatcacgc   1740
tctgggctgc cagggttaaa tcctggccct tccacttacc agctttgtga tgtcagggca   1800
actaactttc tgagcctctg tttcttcatt ttacagtgtg gacacctccc tacctcaggg   1860
tggtcaggat taaatgagat aaccaataca acttgtgtgg gtcagtgcct gcagtacagt   1920
aagtacccag taccagtgat ccacatctca taattactat gacttggcct ggcacagtgg   1980
ctcacgcttg taatcccagc gtgattactt tgggaggcca aggcgggtgg atcacctgag   2040
gtcaggactt caagaccagc ctggccaaca tggtgaaacc ccatctctac taaaaataca   2100
aaaattagct gggcgtggtg gtgggcgcct gtaattgcag ctacttggga ggctgaggca   2160
ggagaaccac ttgaacccag gaggcggagg ttgcagtgag ctgagattgc accattgcac   2220
tccagcctgg gcaataagag ggaaactcca tctcaaaaaa taataataat aattacgatg   2280
acttgtccaa ggagaaaact ggaagccttg gggctcactg ccactctgct cactcaccac   2340
caccagtttt tgtgtttctg gctgacttca gtgccttcat ctcccttcca cagagcatct   2400
cctttacccc acctcagctg cccactccca tggtaatacc tgcatcttgt cacttcacag   2460
ctccaaagcc tcaattccaa gcaccctct ctgcctgac aactcatctt tccagctcac    2520
ttactctggt tactccatgc cagtaagtct ttgaccctg accttaacac agtaacacta   2580
tgcaatac caactcgtgtc ctcaatttcc ttcttacttg actcagattt catgatccag   2640
ctcctcagcc agggccgttc acagacctgg aactccctgg tcccacttct cccctctatc   2700
ttactcacct ggcaaaatcc caaccctgta aaatccagct ctgcccattc agcactgctc   2760
ctgggcagct gactgtggct aagaaaagat gtaccactgt gctcactctt tacaacacat   2820
gcaagtatct aggaggaagg gagggaagga gggagaaaaa agttctcctt tgacgaccac   2880
caccagacct agttctctgt ccgctttgca ggaaaactcc ttaaaagact tacctacttt   2940
tttcaccatt tcttcctgct atcttctttg taactgtaaa ctacaacata caaaaaaatg   3000
cacagaacat acatgtgcag cctgatgaac cccataccac ccaatgtgtg acaacatgtt   3060
ccatctgtcc ttgttttttt ttgttttttgt ttttgagaca gagtctcact ccctcacccg   3120
ggctggagtg cagtggtgcg atgttggctc actacaacct catcctccca ggttcaagcg   3180
attctcgtgc ctcaacctcc tgagtagctg agaccacagg cgtgcggctc cacacctggc   3240
taacttttg tatttttagt agagataggg ttttgccatg ttggccaggc tggtctcaaa   3300
ctcctgacct caagtaatgc gcctgcctca gcctcccaaa gtgctaggat tacagggatg   3360
agccaccata ccggccgcca tcatccttc ttgatcataa tcctctccct ctatacatgc   3420
aagctttatc cttttaagga aatcaactcc ttacatttct ctttagttta tgacctgtgt   3480
atctctcaac aatgcagctt aatttgcag ctttcaaact tgatagaact gaaattgtgc    3540
agtatggatg ctattgggtc agactctttt cacacaatgt tatgtgaagt tgttgcacct   3600
tctctcatgg gcctactcca gtttggcttt ctccaccca ctgaaaccac ggatcttcac    3660
attgccaagc tgctgagca gctctctgtt ctctcatttg gcctgtcagc aacagttgac   3720
acagctgatt cctcctttcc tcttcaaaca ccttcttcat ttgacttctg gacgctccc   3780
ttggttttcc tccttctcac tgtcctttgc ccaactaaat gctggcttgt cctaaggctc   3840
agtccttgac ctcctcttct ccaactatt cctttctctc ctacatctca tccaattcca    3900
```

```
tggcttttt  tttttttttt  ttgacgaagt  cttgctctgt  cacccaggct  ggagtgcagt   3960
ggtatgatct  tggctcaccg  taacctccgc  ctccaggatt  caagcaattc  tcctgcctca   4020
ccctcctgag  tatctgggac  tacaggcacg  caccaccaca  cacggctaat  tttctgtatt   4080
ttttggtaga  gacagggttt  caccatgttg  gccaggctgg  tctcaaactc  ctggcctcaa   4140
gtgatccacc  tgcctcagcc  tcccaaaggg  ctgggattat  aggcatgagc  cactgtgccc   4200
agcctaatcc  tgtggcttta  ataccactt   atatccatca  atggttcccc  aaatttaaat   4260
ctttcccaaa  ttcaaatttc  cgtcctcttc  tctccctaa   gctgctgact  acttacccac   4320
tgcctattca  acatctccac  tagggatatt  taaaaagaat  ctgaaatttc  atttctgatt   4380
ccctctcct   ccccaaagcc  ttcaaatctg  cttctccccc  agtcttccca  tctcagtatt   4440
tccagttgct  caagacaaaa  acctggaagt  ccttctttat  cctcactttc  cttcacgtgc   4500
caactgcaag  ccatcagcga  tctcattttc  tctaccttca  aaatatatca  tgcttccggc   4560
cctgtctcac  cacctccagc  tccagcatcc  tactctaagc  aactcttatt  tctctcctag   4620
attactgaaa  tagcctcaac  tgctctctct  gctccctttc  ttgcccaccc  ccatcatttt   4680
attctctact  caggaggtaa  acttataaga  aacaaaatca  gatcctatca  ttcccctgtt   4740
caaaacctac  ccttggcttc  tcatgagact  tggaataaaa  tccaaaatgg  ctgtcacagc   4800
ctcagggctc  tacatgatgt  gggccctggt  gatcttgctg  acctcatccc  cagtacttta   4860
tcctggctcc  catactccaa  tccctgggc   actcttgctg  gtcctagaat  ctccaagccc   4920
attccctcct  caagacccttt  tccccacagt  tctgaatggc  tcacttcatc  tcatcatcca   4980
gttctctcct  cagggaggtt  tccctgagc   acctctcctc  tcagtcactc  tctatcccct   5040
ttcattgctt  tattgccttc  actgcccta   catgatttcg  gatcacaaaa  tctatttact   5100
cacaagaaaa  taagctccat  gaatctacag  accttttgc   catttccaca  gcagtatgtc   5160
ccatccctag  aatatctggc  acctggttaa  gtgttcagta  catatttgtt  gaatgggtaa   5220
atgaatgaga  gctggaggga  aatccaaact  caggggtgcc  tgtgccacag  caaacactct   5280
ccctctcaca  ccacctggaa  tagagatcag  ctagagcaga  ggctgctaag  agagggaaca   5340
gaggctcctt  gtgacaggga  gactaggatc  agaagtcagg  gaagggacag  ccgggtgaaa   5400
tgactggaaa  gaggagcaat  cactcagcag  taaggcaggt  tcttccaaag  acaaaaagga   5460
cacagagata  agtcagggca  cttccaagga  acccaactac  ctactccaca  ctcccaaatt   5520
tattctgggt  tgggcccttt  ttggttccaa  tatcacctcg  gataccataa  cttgtccaag   5580
gtctcttctt  acctctccca  ccctaaatga  agacgggccc  tgggtcctaa  tcatacattc   5640
cttttcctc   cactgtgagc  tgagacaaag  cccttaagag  gagattctcc  ttggcaacaa   5700
acttaaaggg  ttaaaaccta  gaagaatact  aattcttgct  gagctcctac  tatgatttga   5760
taatcactgt  actacagact  aattactaca  attcaaatgg  tttatataaa  ccacttaaaa   5820
cagtgcctgt  tacatagtaa  gcaccatata  aatactgagt  tttaacaata  ataattgtta   5880
ttattgttat  cactatttgt  caggcattct  tacactctct  taacactatt  cccatcattc   5940
ctcacatcca  ttcttttttt  ttaaagacag  ggtctctatc  agccaggctg  gagtgcagtg   6000
gcacaatcat  agctcactgc  agccttgaac  tcttgggctc  aagtgatcct  cctgcctcag   6060
cctctgaagt  agcagagact  acaggcacat  accaccacac  ttggctagtt  ttctttatct   6120
tttgtaaaga  tggggtttca  ctatgttgcc  cacactagtc  ttgagctcct  ggtctcaagc   6180
aatcctccca  cctcagcctc  ccaaagcgct  gggactatat  aggcatgagc  cctcacacat   6240
```

```
ggccgtcatc cattcttttta ctcaggtatc aatgtcctta tttttaaaat caaagtaact    6300
aagactcaga gtagcaaaat cacttactca agacctcaca gctgagaaga ggtggaattt    6360
aactcaggct gtcatgatcc ttccactgca gcagacgcct cttctgcctt gcccaccgcc    6420
actggcagag atcacccctc agacaccctg gggcctaatg agacctgatc gccctctctc    6480
ttctccgaat atgaaaactc tgtacctcct tggaggccac cacgcacaag ctgccacttc    6540
cttacccaca cagccgatgg tcaccacccc atccttgtag cgctcttggg ttgggccagt    6600
tggctccatt gctgaatcag tctgctgctc caccaggact gctgggccat cctcctcttc    6660
ctcctcctcc ccagagccat taccccaggt ggccccagcc atccccgagc aatcttctc     6720
ccgccagctg ctcaagtcca ctgctcaaag aaggagaaga ttaaagaggt tctccccagg    6780
gctgctgtgc atgatggcac atactgtgcc ctgcacagat tatgtaactg caccctctg     6840
gagttgtaca gtgccaacct aaataagagc aggtcagaga atctcccaaa agtcatttga    6900
ccctaccctc cctggaatca cgcacgtttc tctgagcttc tgaaaagtac tgggaaggct    6960
aaaggcagca agccactgag gctcctgact acctgctgcc tctcgtccca ccaagtcagt    7020
ctgctcctta ttctgtccct tccctggcc tcttgcacat atccaccata gaggggttgg     7080
cttcaggaaa ggtgagcaaa atgattctgc atctttggtc tcccccatgt cctcctacag    7140
ccctcctcta agggccacat acctttcccc acagtgatgg cttcacaggc tctcagcaac    7200
tgctctggcc ccagggcccg agtccatcct ctccccgcc tccgactctt cttcaagact      7260
gagatcagag ggcacaaaag gatgggcaca cgggcttagg cctctcatct ctcccaccac    7320
ccttaggccc aagaccaggt gcccccttgt caataagcct ctctgttctc ccctttgtcc    7380
cctgccaact cacctctccc aagttgccct ctctcattgc ccactcacca ctactaggat    7440
cctgtggggt gcggggtcc cgaggaaaag aggtgaaaag gacgacgtgg agctggggat     7500
agtgttgatg gaaataatgc ttccaggcaa ccacaagagc tggcggggcc agatccacct    7560
tgttcaaaac cagcaccagg gccagtccaa gttctccagt cacatactca taaagtgctg    7620
gcgggaaatt cacaacctag gacagagttg ataagaggat ggagcagtga aagtcaaccc    7680
agagttctct gcctccagct ccccactcag caggtgtagc tcagagacaa ggccctggtg    7740
gtagcagact ctgggctaaa actataaac cagacaaact gaaaaacaaa gacaaaacag     7800
gggttagtaa tacttctgag tctcagaggg cttcctatag gtcatgatta gagatggaaa    7860
tgaacccaaa acaagacaag gaaacagcat cacttagcac actgaggtaa aggctgggat    7920
cggaaacagg gatgggggtt agggtagaaa ttagtctgct tttttgtgtg tgcacaacta    7980
tgtaagtgtg tacacgtgca tatatgcatg catgcaagta cgtgcacatg tgtgcatgtt    8040
tgtgtgttaa tgtgactgtg aacatgtgtg caaacatgcc tgtgtatatt gatgtgcaca    8100
tgatgtacgt gtgagtatgt gtgtgtacat attattaagg acctccaacc taaatggtcc    8160
tcacagacct ccctttctcc cactggagga caagagtgaa gttgcagagc taggattcac    8220
acagggcagt ccagcagcag tctacagcct taactactac tctagcattc caggtgggtt    8280
ctgtagcaac tgatgtggca gtgctagaga aatgagataa ggaagaaagg gcatctttgg    8340
gctgggcagg aggaagtccc cagctgcatt catagaatcc ctggagctcc aacacttgga    8400
ttttctattg gtctgtgatg agctaaagga caggacatgg ctgttttgaa gagaagagtg    8460
agctggccaa gggaggaatg acaggctata agagaataaa aaactgagtt cctaactgcg    8520
gacatcagca ctaggtagag attagaaaga caggaagata gatacctctc tgtctcccaa    8580
ctcttgcctc tgacctttgc ccctgaaaaa cctttctccc tcctccttgc ccacccttat    8640
```

```
ccctagtact cactggatgt cggatatcag tgataagcag gacgatgtca gacatctcta    8700
acacccgcca cagctgcctc catgtctaaa aagacaggat caggaagaga aactgaaaac    8760
agagtccctc tccagcctga tcccaaacca atttgaccat aggtcactat gccccactcc    8820
tgtccctaga gtacactgtc acctccagat tgtgctcaaa gtagctgagt ttctcagagg    8880
agtaagcccc atgaatcttc ccaagatagt cttggaagct ccgttcctct tggctcatta    8940
gttgctcctt ggacatctca tagctccaag gaggacgtcg aggaaagtcc agaactggga    9000
attcaggaaa aagtccaagt gtgaggaaat cttcaggatt caagagtaca tcccagaccc    9060
ctccttcctc acagtcggct tttacctttc caaactcctt ccccagccca atgcctgtct    9120
tgctctcact cacctgagcc aggctgatac acctcccgga tgtccagctc caacaactca    9180
gcactgaccg gctgtagaac ttgctcccgg gctgctctct ttctcctctc tacctcctcc    9240
ctgctgtctc tctcaaaatg cagtcggtat ctaagggaac agggaccgag acatccagag    9300
caatcctgtg gccacaaact cctatttct cccctcttgt acaatcaact tcgcaaacca    9360
ttctctccag agtcgttcaa gtctcctctc tcaagtcaga cttcccccaa gtccttcttt    9420
caggcaatac tcagccttct ccttctaaaa gcccaactct ctccagcccc tctggaaagg    9480
aagactgtgg cccgctgtgg ggagccgagt ggctagcgga gaactgtggc atcccaggcc    9540
caccgtcttc accagtagca gcccgctttc ccccaaagct ctgacttccg ggtaggcggg    9600
aaagccggga ccagcgcccc ctcccaccct caccgatttg ggtcgtagcc tcgtggaccc    9660 agccctgag aaggctgctg gttaagcctg cggatatgat gggtcacaga ctccccgtcc    9720
gaggtgtcgg tctgttcctc tcgccgctcc cggctcccgc tgcggctgtt ggaactggag    9780
cgcagcccat cttgaagccc tgcggggagg ggccggtgac gccagtgctg gccagctctc    9840
aggggccata agaccctctc ccccatcggc ctgactccct ttcatcccac tcaacttctt    9900
ccgatgttca gtcctcccag acaccctatt tgggaccctc ccggatgtgc gtgggggag    9960 tcactccttc agggagcagt ggggacggcg ccccgtgcta gctggaggga ttcccctccc   10020
ccaactctcc atccttcccc accccttcca gatgtagggg gggtggggga tcccctccgc   10080
gataggccgc gagggttgac gcggtcccac gaccccctcc cacgatcccc agaggtgcag   10140
cgggcacacc cctccttcca gatgtgcgga agcccgagcc ccgccccctc ctcccgctcc   10200
cgcactgacc tctcttccgc tcccgtttgt cctgcaactg cttcttcttc tgcttcacgc   10260
tgaatggctt cttcctcggc atggcccgga ccagtcacct ggcccgccct ccgccgagct   10320
cccgccgcct caactgactg ccccccgggg cagccccgc cgcaggggcc cgggacccta   10380
gaggaggcgg ggctagcagg tgacgtcagc gggcgggccc gacagaatta ccgccgcggc   10440
ggcgatggaa ggcggacggg ggagatatag tcacttccct ccagga               10486
```

<210> SEQ ID NO 7
<211> LENGTH: 33
<212> TYPE: DNA
<213> ORGANISM: Artificial
<220> FEATURE:
<223> OTHER INFORMATION: Synthetic Primer
<220> FEATURE:
<221> NAME/KEY: misc_feature
<222> LOCATION: (32)..(33)
<223> OTHER INFORMATION: The bond between position 32 and 33 is a
      phosphorothioate bond

<400> SEQUENCE: 7

```
acactctttc cctacacgac gctcttccga tct                               33
```

<210> SEQ ID NO 8
<211> LENGTH: 33
<212> TYPE: DNA
<213> ORGANISM: Artificial
<220> FEATURE:
<223> OTHER INFORMATION: Synthetic Primer

<400> SEQUENCE: 8
gatcggaaga gctcgtatgc cgtcttctgc ttg                                   33

<210> SEQ ID NO 9
<211> LENGTH: 44
<212> TYPE: DNA
<213> ORGANISM: Artificial
<220> FEATURE:
<223> OTHER INFORMATION: Synthetic Primer

<400> SEQUENCE: 9
aatgatacgg cgaccaccga gatctacact ctttccctac acga                       44

<210> SEQ ID NO 10
<211> LENGTH: 21
<212> TYPE: DNA
<213> ORGANISM: Artificial
<220> FEATURE:
<223> OTHER INFORMATION: Synthetic Primer

<400> SEQUENCE: 10
caagcagaag acggcatacg a                                                21

<210> SEQ ID NO 11
<211> LENGTH: 35
<212> TYPE: DNA
<213> ORGANISM: Artificial
<220> FEATURE:
<223> OTHER INFORMATION: Synthetic Primer

<400> SEQUENCE: 11
aatgatacgg cgaccaccga gaaaaacgcc agcaa                                 35

<210> SEQ ID NO 12
<211> LENGTH: 32
<212> TYPE: DNA
<213> ORGANISM: Artificial
<220> FEATURE:
<223> OTHER INFORMATION: Synthetic Primer

<400> SEQUENCE: 12
caagcagaag acggcatacg atccgacagc tt                                    32

<210> SEQ ID NO 13
<211> LENGTH: 309
<212> TYPE: DNA
<213> ORGANISM: Homo sapiens

<400> SEQUENCE: 13
ctcttcttca agactgagat cagagggcac aaaaggatgg gcacacgggc ttaggcctct       60
catctctccc accacccttc ggcccaagac caggtgcccc cttgtcaata agcctctctg      120
ttctcccctt tgtcccctgc caactcacct ctcccaagtt gccctctctc attgcccact      180
caccactact aggatcctgt ggggtgcggg ggtcccgagg aaaagaggtg aaaaggacga      240
cgtggagctg gggatagtgt tgatggaaat aatgcttcca gcaaccaca agagctggcg      300

```
gggccagat                                                                    309
```

<210> SEQ ID NO 14
<211> LENGTH: 239
<212> TYPE: DNA
<213> ORGANISM: Homo sapiens

<400> SEQUENCE: 14

```
tgtaagaatg cctgacaaat agtgataaca ataataacaa ttattattgt taaaactcag     60
tatttatatg gtgcttacta tgtaacaggc actgttttaa gtggtttata taaaccattt    120
gaattgtagt aattagtctg tagtacagtg attatcaaat catagtagga gctcagcaag    180
aattagtatt cttctaggtt ttaacccttt aagtttgttg ccaaggagaa tctcctctt     239
```

<210> SEQ ID NO 15
<211> LENGTH: 503
<212> TYPE: DNA
<213> ORGANISM: Homo sapiens

<400> SEQUENCE: 15

```
ggccatgtgt gagggctcat gcctatatag tcccagcgct ttgggaggct gaggtgggag     60
gattgcttga ccaggagc tcaagactag tgtgggcaac atagtgaaac ccatctttta       120
caagagataa agaaaactag ccaagtgtgg tggtatgtgc ctgtagtctc tgctacttca    180
gaggctgagg caggaggatc acttgagccc aagagttcaa ggctgcagtg agctatgatt    240
gtgccactgc actccagcct ggctgataga gaccctgtct ttaaaaaaaa agaatggatg    300
tgaggaatga tgggaatagt gttaagagag tgtaagaatg cctgacaaat agtgataaca    360
ataataacaa ttattattgt taaaactcag tatttatatg gtgcttacta tgtaacaggc    420
actgttttaa gtggtttata taaaccattt gaattgtagt aattagtctg tagtacagtg    480
attatcaaat catagtagga gct                                            503
```

<210> SEQ ID NO 16
<211> LENGTH: 405
<212> TYPE: DNA
<213> ORGANISM: Homo sapiens

<400> SEQUENCE: 16

```
ccatgtgcct ggcttcgccc cacctggttt cagctgctct tccttacctg cctcgccttt     60
tacccttccc tgtctccttt cctctcctca gagattctgc cattgatgaa gctgctgtcc    120
actcacccct agattttgt tgcatagcag taagatctct ggcctggaat gttttgggga    180
aaactggaag gactgtgtta tgggagtggg agtataactg gtacctggtt aatgctttcc    240 cttttccatta ttcttttctt cctccagcct gggcagagaa acgtggttac aagacagcca    300
aggcggctcg gaatgatgtg tacagagcag ccaacagtct cttgcggctg gcagtggacg    360
gccgcctcag cctgtgtttt catcccccag gctacagtga acaga                    405
```

<210> SEQ ID NO 17
<211> LENGTH: 297
<212> TYPE: DNA
<213> ORGANISM: Homo sapiens

<400> SEQUENCE: 17

```
gaggaactca gcactcatcc tcacccagca gggcataagg gtttcggcca gccaggctgg     60
accctggagc cgaggttggg gtctcctcat cccttctcc ctcctcatcc gcatcccggt     120
cctcctctcc ctcctcccca caggagctgc tcagctcttc ctcttcctcc tcctcctcgt    180
```

```
cacctgctgg ccccaccctg ccctgcaaaa ccaccagctc cgtggtctct ggatgggact    240
cccaggtgcc tggggaacca aaacaagaaa aaaatggagg agagtttga gcaagaa       297
```

<210> SEQ ID NO 18
<211> LENGTH: 411
<212> TYPE: DNA
<213> ORGANISM: Homo sapiens

<400> SEQUENCE: 18

```
cgaggaactc agcactcatc ctcacccagc agggcataag ggtttcggcc agccaggctg    60
gaccctggag ccgaggttgg ggtctcctca tccccttctc cctcctcatc cgcatcccgg   120
tcctcctctc cctcctcctc acaggagctg ctcagctctt cctcttcctc ctcctcctcg   180
tcacctgctg gccccacccct gccctgcaaa accaccagct ccgtggtctc tggatgggac   240
tcccaggtgc ctggggaacc aaaacaagaa aaaaatggag agagtttg agcaagaact    300 aaagccaagg aaagatgggg aagaggcaaa gactaggaat aacaataatc tttagagctg    360
ctggcattca ttcattcatc cattcattca acttcctatg tgcagattgc t            411
```

<210> SEQ ID NO 19
<211> LENGTH: 390
<212> TYPE: DNA
<213> ORGANISM: Homo sapiens

<400> SEQUENCE: 19

```
ctgagtagct gagaccacag gcgtgcggct ccacacctgg ctaactttt gtatttttag    60 tagagatagg gttttgccat gttggccagg ctggtctcaa actcctgacc tcaagtaatg   120
cgcctgcctc agcctcccaa agtgctagga ttacagggat gagccaccat accggccgcc   180
actcatcctt cttgatcata atcctctccc tctatacatg caagctttat ccttttaagg   240
aaatcaactc cttacatttc tctttagttt atgacctgtg tatctctcaa caatgcagct   300
taattttgca gctttcaaac ttgatagaac tgaaattgtg cagtatggat gctattgggt   360
cagactcttt tcacacaatg ttatgtgaag                                    390
```

<210> SEQ ID NO 20
<211> LENGTH: 282
<212> TYPE: DNA
<213> ORGANISM: Homo sapiens

<400> SEQUENCE: 20

```
taaaaaaaaa gccatggaat tggatgagat gtaggagaga aaggaaatag ttggagaaga    60
ggaggtcaag gactgagcct taggacaagc cagcatttag ttgggcaaag gacagtgaga   120
aggaggaaaa ccaagggagc gtcccagaag tcaaatgaag aaggtgtttg aagaggaaag   180
gaggaatcag ctgtgtcaac tgttgctgac aggccaaatg agagaacaga gagctgctca   240
gcaggcttgg caatgtgaag atccgtggtt tcagtgggt gg                       282
```

<210> SEQ ID NO 21
<211> LENGTH: 503
<212> TYPE: DNA
<213> ORGANISM: Homo sapiens

<400> SEQUENCE: 21

```
cgaggaactc agcactcatc ctcacccagc agggcataag ggtttcggcc agccaggctg    60
gaccctggag ccgaggttgg ggtctcctca tccccttctc cctcctcatc cgcatcccgg   120
```

| | |
|---|---|
| tcctcctctc cctcctcctc acaggagctg ctcagctctt cctcttcctc ctcctcctcg | 180 |
| tcacctgctg gccccaccct gccctgcaaa accaccagct ccgtggtctc tggatgggac | 240 |
| tcccaggtgc ctggggaacc aaaacaagaa aaaatggag gagagttttg agcaagaact | 300 |
| aaagccaagg aaagatgggg aagaggcaaa gactaggaat aacaataatc tttagagctg | 360 |
| ctggcattca ttcattcatc cattcattca acttcctatg tgcagattgc tgaacagaac | 420 |
| cttttgtgcgc atcaacttca atctttacaa tcactatgct aagggtcaat tattaccctc | 480 |
| agtttgcaga tcaggaaaat atc | 503 |

<210> SEQ ID NO 22
<211> LENGTH: 293
<212> TYPE: DNA
<213> ORGANISM: Homo sapiens

<400> SEQUENCE: 22

| | |
|---|---|
| cactgcactc cagcctggct gatagagacc ctgtctttaa aaaaaagaa tggatgtgag | 60 |
| gaatgatggg aatagtgtta agagagtgta agaatgcctg acaaatagtg ataacaataa | 120 |
| taacaattat tattgttaaa actcagtatt tatatggtgc ttactatgta acaggcactg | 180 |
| ttttaagtgg tttatataaa ccatttgaat tgtagtaatt agtctgtagt acagtgatta | 240 |
| tcaaatcata gtaggagctc agcaagaatt agtattcttc taggttttaa ccc | 293 |

<210> SEQ ID NO 23
<211> LENGTH: 232
<212> TYPE: DNA
<213> ORGANISM: Homo sapiens

<400> SEQUENCE: 23

| | |
|---|---|
| cctacccgga agtcagagct ttgggggaaa gcgggctgct actggtgaag acggtgggcc | 60 |
| tgggatgcca cagttctccg ctagccactc ggctccccac agcgggccgc agtcttcctt | 120 |
| tccagagggg ctggagagag ttgggctttt agaaggagaa ggctgagtat tgcctgaaag | 180 |
| aaggacttgg gggaagtctg acttgagaga ggagacttga acgactctgg ag | 232 |

<210> SEQ ID NO 24
<211> LENGTH: 315
<212> TYPE: DNA
<213> ORGANISM: Homo sapiens

<400> SEQUENCE: 24

| | |
|---|---|
| tatcagccag gctggagtgc agtggcacaa tcatagctca ctgcagcctt gaactcttgg | 60 |
| gctcaagtga tcctcctgcc tcagcctctg aagtagcaga gactacaggc ataccacc | 120 |
| acacttggct agttttcttt atcttttgta aagatggggt ttcactatgt tgcccacact | 180 |
| agtcttgagc tcctggtctc aagcaatcct cccacctcag cctcccaaag cgctgggact | 240 |
| atataggcat gagccctcac acatggccgt catccattct tttactcagg tatcaatgtc | 300 |
| cttatttta aaatc | 315 |

<210> SEQ ID NO 25
<211> LENGTH: 325
<212> TYPE: DNA
<213> ORGANISM: Homo sapiens

<400> SEQUENCE: 25

| | |
|---|---|
| gtgaggtctt gagtaagtga ttttgctact ctgagtctta gttactttga ttttaaaaat | 60 |
| aaggacattg ataccctgagt aaaagaatgg atgacggcca tgtgtgaggg ctcatgccta | 120 |

```
tatagtccca gcgctttggg aggctgaggt gggaggattg cttgagacca ggagctcaag    180
actagtgtgg gcaacatagt gaaacccat ctttacaaaa gataaagaaa actagccaag     240
tgtggtggta tgtgcctgta gtctctgcta cttcagaggc tgaggcagga ggatcacttg    300
agcccaagag ttcaaggctg cagtg                                          325
```

```
<210> SEQ ID NO 26
<211> LENGTH: 315
<212> TYPE: DNA
<213> ORGANISM: Homo sapiens

<400> SEQUENCE: 26
tatcagccag gctggagtgc agtggcacaa tcatagctca ctgcagcctt gaactcttgg     60
gctcaagtga tcctcctgcc tcagcctctg aagtagcaga gactacaggc acataccacc    120
acacttggct agttttcttt atcttttgta aagatggggt ttcactatgt tgcccacact    180
agtcttgagc tcctggtctc aagcaatcct cccacctcag cctcccaaag cgctgggact    240
atataggcat gagccctcac acatggccgt catccattct tttactcagg tatcaatgtc    300 cttatttta aaatc                                                      315
```

```
<210> SEQ ID NO 27
<211> LENGTH: 384
<212> TYPE: DNA
<213> ORGANISM: Homo sapiens

<400> SEQUENCE: 27
cgaggaactc agcactcatc ctcacccagc agggcataag ggtttcggcc agccaggctg     60
gaccctggag ccgaggttgg ggtctcctca tccccttctc cctcctcatc cgcatcccgg    120
tcctcctctc cctcctcctc acaggagctg ctcagctctt cctcttcctc ctcctcctcg    180
tcacctgctg gccccaccct gccctgcaaa accaccagct ccgtggtctc tggatgggac    240
tcccaggtgc ctggggaacc aaaacaagaa aaaaatggag gagagttttg agcaagaact    300
aaagccaagg aaagatgggg aagaggcaaa gactaggaat aacaataatc tttagagctg    360
ctggcattca ttcattcatc catt                                           384
```

```
<210> SEQ ID NO 28
<211> LENGTH: 306
<212> TYPE: DNA
<213> ORGANISM: Homo sapiens

<400> SEQUENCE: 28
cgaggaactc agcactcatc ctcacccagc agggcataag ggtttcggcc agccaggctg     60
gaccctggag ccgaggttgg ggtctcctca tccccttctc cctcctcatc cgcatcccgg    120
tcctcctctc cctcctcctc acaggagctg ctcagctctt cctcttcctc ctcctcctcg    180
tcacctgctg gccccaccct gccctgcaaa accaccagct ccgtggtctc tggatgggac    240
tcccaggtgc ctggggaacc aaaacaagaa aaaaatggag gagagttttg agcaagaact    300
aaagcc                                                               306
```

```
<210> SEQ ID NO 29
<211> LENGTH: 255
<212> TYPE: DNA
<213> ORGANISM: Homo sapiens

<400> SEQUENCE: 29
```

```
cagtactttc ctcaatgtcc caccttctct ctttccctta cccaccctcc ccgtcatacc    60
tgcaactgcc taggcagaag agatgggaag atgaggcctg ggcagtcaca gagcttcaca   120
gagggggtaa gaaagtaggt ctgaaagtat cgggtatggc ccggggttct ggagacactc   180
acgactttcc gccccaccag cccattgatc agcgaggact ttcccacatt agggaaacct   240
gaggaaggca aggaa                                                    255

<210> SEQ ID NO 30
<211> LENGTH: 170
<212> TYPE: DNA
<213> ORGANISM: Homo sapiens

<400> SEQUENCE: 30
aaccccatct ctactaaaaa tacaaaaatt agctgggcgt ggtggtgggc gcctgtaatt    60
gcagctactt gggaggctga ggcaggagaa ccacttgaac ccaggaggcg gaggttgcag   120
tgagctgaga ttgcaccatt gcactccagc ctgggcaata gagggaaac                170

<210> SEQ ID NO 31
<211> LENGTH: 222
<212> TYPE: DNA
<213> ORGANISM: Homo sapiens

<400> SEQUENCE: 31
cggacatcag cactaggtag agattagaaa gacaggaaga tagatacctc tctgtctccc    60
aactcttgcc tctgaccttt gcccctgaaa aacctttctc cctcctcctt gcccaccctt   120
atccctagta ctcactggat gtcggatatc agtgataagc aggacgatgt cagacatctc   180
taacacccgc cacagctgcc tccatgtcta aaaagacagg at                      222

<210> SEQ ID NO 32
<211> LENGTH: 390
<212> TYPE: DNA
<213> ORGANISM: Homo sapiens

<400> SEQUENCE: 32
ttgacgcggt cccacgaccc cctcccacga tccccagagg tgcagcgggc acacccctcc    60
ttccagatgt gcggaagccc gagccccgcc ccctcctccc gctcccgcac tgacctctct   120
tccgctcccg tttgtcctgc aactgcttct tcttctgctt cacgctgaat ggcttcttcc   180
tcggcatggc ccggaccagt cacctggccc gccctccgcc gagctcccgc cgcctcaact   240
gactgccccc cggggcagcc cccgccgcag gggcccggga ccctagagga ggcgggggcta   300 gcaggtgacg tcagcgggcg ggcccgacag aattaccgcc gcggcggcga tggaaggcgg   360 acggggga ga tatagtcact tccctccagg                                   390

<210> SEQ ID NO 33
<211> LENGTH: 236
<212> TYPE: DNA
<213> ORGANISM: Homo sapiens

<400> SEQUENCE: 33
gcccacagca gtgtagggct cctggatctg ggcgatagg g tagatccccg ccagaacctg    60
agggaaatga gcactcagta ctttcctcaa tgtcccacct tctctctttc ccttacccac   120
cctccccgtc atacctgcaa ctgcctaggc agaagagatg ggaagatgag gcctgggcag   180
tcacagagct tcacagaggg ggtaagaaag taggtctgaa agtatcgggt atggcc       236
```

<210> SEQ ID NO 34
<211> LENGTH: 293
<212> TYPE: DNA
<213> ORGANISM: Homo sapiens

<400> SEQUENCE: 34

| gctgccttta gccttcccag tacttttcag aagctcagag aaacgtgcgt gattccaggg | 60 |
| agggtagggt caaatgactt ttgggagatt ctctgacctg ctcttattta ggttggcact | 120 |
| gtacaactcc agagggtgcc agttacataa tctgtgcagg gcacagtatg tgccatcatg | 180 |
| cacagcagcc ctggggagaa cctctttaat cttctccttc tttgagcagt ggacttgagc | 240 |
| agctggcggg agaagattgc tcgggatgtg gctggggcca cctggggtaa tgg | 293 |

<210> SEQ ID NO 35
<211> LENGTH: 160
<212> TYPE: DNA
<213> ORGANISM: Homo sapiens

<400> SEQUENCE: 35

| gaggtggaat ttaactcagg ctgtcatgat ccttccactg cagcagacgc tcttctgcc | 60 |
| ttgcccaccg ccactggcag agatcacccc tcagacaccc tggggcctaa tgagacctga | 120 |
| tcgccctctc tcttctccga atatgaaaac tctgtacctc | 160 |

<210> SEQ ID NO 36
<211> LENGTH: 193
<212> TYPE: DNA
<213> ORGANISM: Homo sapiens

<400> SEQUENCE: 36

| tgctgctcca ccaggactgc tgggccatcc tcctcctcct cctcctcccc agagccatta | 60 |
| ccccaggtgg ccccagccac atcccgagca atcttctccc gccagctgct caagtccact | 120 |
| gctcaaagaa ggagaagatt aaagaggttc tccccagggc tgctgtgcat gatggcacat | 180 |
| actgtgccct gca | 193 |

<210> SEQ ID NO 37
<211> LENGTH: 187
<212> TYPE: DNA
<213> ORGANISM: Homo sapiens

<400> SEQUENCE: 37

| atggctgtca cagcctcagg gctctacatg atgtgggccc tggtgatctt gctgacctca | 60 |
| tccccagtac tttatcctgg ctcccatact ccaatcccct gggcactctt gctggtccta | 120 |
| gaatctccaa gcccattccc tcctcaagac ccttttcccca cagttctgaa tggctcactt | 180 |
| catctca | 187 |

<210> SEQ ID NO 38
<211> LENGTH: 188
<212> TYPE: DNA
<213> ORGANISM: Homo sapiens

<400> SEQUENCE: 38

| ctttgacgac caccaccaga cctagttctc tgtccgcttt gcaggaaaac tccttaaaag | 60 |
| acttacctac tttttcacc atttcttcct gctatcttct ttgtaactgt aaactacaac | 120 |
| atacaaaaaa atgcacagaa catacatgtg cagcctgatg aaccccatac cacccaatgt | 180 |
| gtgacaac | 188 |

END MODIFICATION TO PREVENT OVER-REPRESENTATION OF FRAGMENTS

FIELD OF THE INVENTION

The invention relates to a method of preparing a 5' and 3' modified library of template polynucleotides and also the use of the 5' and 3' modified library of templates in methods of solid-phase nucleic acid amplification. In particular, the invention relates to a method of preparing a 5' and 3' modified library of template polynucleotides which have common sequences at their 5' ends and at their 3' ends, wherein over-representation of "end" sequences of the primary polynucleotide molecules from whence the 5' and 3' modified library is generated is greatly reduced or prevented.

BACKGROUND TO THE INVENTION

Molecular biology and pharmaceutical drug development now make intensive use of nucleic acid analysis. The most challenging areas are whole genome sequencing, single nucleotide polymorphism detection, screening and gene expression monitoring, which typically require analysis of large amounts of nucleic acid.

One area of technology which revolutionised the study of nucleic acids was the development of nucleic acid amplification techniques, such as the polymerase chain reaction (PCR). Amplification reactions, such as PCR, can enable the user to specifically and selectively amplify a particular target nucleic acid of interest from a complex mixture of nucleic acids. However, there is also an ongoing need for nucleic acid amplification techniques which enable simultaneous amplification of complex mixtures of templates of diverse sequence, such as genomic DNA fragments (e.g. "whole genome" amplification) or cDNA libraries, in a single amplification reaction.

PCR amplification cannot occur in the absence of annealing of forward and reverse amplification primers to primer binding sequences in the template to be amplified under the conditions of the annealing steps of the PCR reaction, i.e. if there is insufficient complementarity between primers and template. Some prior knowledge of the sequence of the template is therefore required before one can carry out a PCR reaction to amplify a specific template, unless random primers are used with a consequential loss of specificity. The user must usually know the sequence of at least the primer-binding sites in the template in advance so that appropriate primers can be designed, although the remaining sequence of the template may be unknown. The need for prior knowledge of the sequence of the template increases the complexity and cost of PCR amplification of complex mixtures of templates, such as genomic DNA fragments.

WO 98/44151 and WO 00/18957 both describe methods of forming polynucleotide arrays based on "solid-phase" nucleic acid amplification wherein the amplification products are immobilised on a solid support in order to form arrays comprised of nucleic acid clusters or "colonies". Each cluster or colony on such an array is formed from a plurality of identical immobilised polynucleotide strands and a plurality of identical immobilised complementary polynucleotide strands. The arrays so-formed are generally referred to herein as "clustered arrays" and their general features will be further understood by reference to WO 98/44151 or WO 00/18957, the contents of both documents being incorporated herein in their entirety by reference.

As aforesaid, the solid-phase amplification methods of WO 98/44151 and WO 00/18957 are essentially carried out on a solid support. Like any amplification reaction these methods require the use of forward and reverse amplification primers (which may be identical or different) capable of annealing to a template to be amplified. In the methods of WO 98/44151 and WO 00/18957 both primers are immobilised on the solid support at the 5' end. Other forms of solid-phase amplification are known in which only one primer is immobilised and the other is present in free solution (Mitra, R. D and Church, G. M., Nucleic Acids Research, 1999, Vol. 27, No. 24).

In common with all amplification techniques, solid-phase PCR amplification requires the use of forward and reverse amplification primers which include "template-specific" nucleotide sequences which are capable of annealing to sequences in the template to be amplified, or the complement thereof, under the conditions of the annealing steps of the amplification reaction. The sequences in the template to which the primers anneal under conditions of the amplification reaction may be referred to herein as "primer-binding" sequences.

Certain embodiments of the methods described in WO 98/44151 and WO 00/18957 make use of "universal" primers to amplify templates comprising a variable target portion that it is desired to amplify flanked 5' and 3' by common or "universal" primer binding sequences. The "universal" forward and reverse primers include sequences capable of annealing to the "universal" primer binding sequences in the template construct. The variable target portion may itself be of known, unknown or partially known sequence. This approach has the advantage that it is not necessary to design a specific pair of primers for each target to be amplified; the same primers can be used for amplification of different targets provided that each target is modified by addition of the same universal primer-binding sequences to its 5' and 3' ends. The variable target sequence can therefore be any DNA fragment of interest. An analogous approach can be used to amplify a mixture of targets, such as a plurality or collection of target nucleic acid molecules (e.g. genomic DNA fragments), using a single pair of universal forward and reverse primers, provided that each target molecule in the collection is modified by the addition of the same universal primer-binding sequences.

Such "universal primer" approaches to PCR amplification, and in particular solid-phase PCR amplification, are advantageous since they enable multiple template molecules of the same or different, known or unknown sequence to be amplified in a single amplification reaction, which may be carried out on a solid support bearing a single pair of "universal" primers. Simultaneous amplification of a mixture of templates of different sequences by PCR would otherwise require a plurality of primer pairs, each pair being complementary to each unique template in the mixture. The generation of a plurality of primer pairs for each individual targets is not a viable option for complex mixtures of targets.

The addition of universal priming sequences onto the ends of targets to be amplified can be achieved by a variety of methods known to those skilled in the art. For example, a universal primer consisting of a universal sequence at its 5' end and a degenerate sequence at its 3' end can be used in a PCR (DOP-PCR, eg PNAS 1996 vol 93 pg 14676-14679) to amplify fragments randomly from a complex target or a complex mixture of targets. The degenerate 3' portion of the primer anneals at random positions on DNA and can be extended to generate a copy of the template that has the universal sequence at its 5' end.

Alternatively, adapters that contain universal priming sequences can be ligated onto the ends of targets. The adapters may be single-stranded or double-stranded. If double-stranded, they may have overhanging ends that are complementary to overhanging ends on the target molecules that have been generated with a restriction endonuclease. Alternatively, the double-stranded adapters may be blunt, in which case the targets are also blunt ended. The blunt ends of the targets may have been formed during a process to shear the DNA into fragments, or they may have been formed by an end repair reaction, as would be well known to those skilled in the art. The ends of the targets may be treated to obtain a single 3'-overhang.

A single adapter or two different adapters may be used in a ligation reaction with targets. If a target has been manipulated such that its ends are the same, i.e. both are blunt or both have the same overhang, then ligation of a single compatible adapter will generate a target sequence with that adapter on both ends. However, if two compatible adapters, adapter A and adapter B, are used, then three permutations of ligated products are formed: target with adapter A on both ends, target with adapter B on both ends, and target with adapter A on one end and adapter B on the other end. This last product is, under some circumstances, the only desired product from the ligation reaction and consequently additional purification steps are necessary following the ligation reaction to purify it from the ligation products that have the same adapter at both ends.

SUMMARY OF THE INVENTION

In a first aspect the invention provides a method of generating a 5' and 3' modified library of template polynucleotide molecules from one or more primary polynucleotide molecules, wherein said primary polynucleotide molecules are modified primary polynucleotide molecules comprising a modification at or near each 5'-terminus that prevents ligation to their 5'-termini; said method comprising the step of:
  a) Fragmenting the modified primary polynucleotide molecules to produce target polynucleotide duplexes, wherein the target polynucleotide duplexes comprise modified target polynucleotide duplexes comprising the modification at or near a 5' terminus and unmodified target polynucleotide duplexes comprising two ligatable termini;
  b) ligating adapter polynucleotides to the two ligatable termini of the unmodified target polynucleotide duplexes to form one or more adapter-target-adapter constructs;
  c) carrying out an amplification reaction, wherein a primer oligonucleotide is annealed to both 5'-terminal adapter portions of each of the adapter-target-adapter constructs and extended by sequential addition of nucleotides to form extension products complementary to each strand of each of the adapter-target constructs, wherein the extension products have common sequences at their 5' ends and common sequences at their 3' ends and collectively provide a 5' and 3' modified library of template polynucleotide molecules; wherein said method prevents the over-representation of the sequences at either end of the primary polynucleotide molecules in the 5' and 3' modified library of template polynucleotide molecules.

In an aspect of the method, the modification at or near the 5' terminus of the primary polynucleotide molecules is introduced using an amplification reaction. Such amplification reactions may comprise one or more modified amplification primers. In a further embodiment of the method, the modified amplification primers comprise a 5'-amino or 5'-biotin modification. It is also envisioned that modified amplification primers may comprise a modification that prevents nucleotide polymerase mediated copying of the full length of the primer. Modified amplification primers may also comprise an abasic site.

In an embodiment of the method wherein the primary polynucleotides are double stranded, the modification at or near the 5' terminus of the primary polynucleotides may be introduced using an enzyme. In a further aspect, the modification is a modified deoxynucleoside triphosphate introduced using a nucleotide polymerase. In yet a further aspect, the modification is a dideoxynucleoside triphosphate introduced using a terminal transferase.

In accordance with an aspect of the method, fragmentation of the primary polynucleotide molecules may be achieved by sonication or nebulization.

In an aspect of the invention, the primary polynucleotide molecules are DNA molecules. In an embodiment of the method, the modified primary polynucleotide molecules are generated by polymerase chain reaction (PCR).

In an aspect of the method, the modified primary polynucleotide molecules are at least 5000 base pairs in length.

In another aspect of the method, at least one of the amplification primers extends beyond the 5'-bases of the adapter.

In yet another aspect of the method, the adapter contains a double stranded region and at least one single stranded region.

The present method may further comprise the steps of:
  (d) preparing clusters from the 5' and 3' modified library of template polynucleotide molecules; and
  (e) sequencing the clusters by sequencing by synthesis.

The present invention also encompasses a 5' and 3' modified library of template polynucleotide molecules prepared using an aspect of the method of the invention. The present invention also encompasses an array comprising a 5' and 3' modified library of template polynucleotide molecules prepared using an aspect of the method of the invention. The present invention further envisions methods of using the 5' and 3' modified library prepared using an aspect of the method of the invention in sequencing and methods of using the array comprising a 5' and 3' modified library of template polynucleotide molecules prepared using an aspect of the method of the invention in sequencing.

DETAILED DESCRIPTION OF THE INVENTION

In a first aspect the invention provides a method of generating a 5' and 3' modified library of template polynucleotide molecules from one or more primary polynucleotide molecules characterised in that said method prevents over-representation of the sequences at either end of the primary polynucleotide molecules in the 5' and 3' modified library of template polynucleotide molecules. Accordingly, the method of the present invention addresses the problem of over-representation of terminal sequences of primary polynucleotides in 5' and 3' modified libraries generated therefrom.

UK Application Patent application Number 0522310.2, herein incorporated by reference, is a method that uses a single adapter in a ligation reaction to generate a 5' and 3' modified library of template polynucleotides each of which have common, but different, universal primer sequences at their 5' and 3' ends. The method can be applied to preparing simple or complex mixes of templates for amplification, for example a solid surface, using primer sequences, with no prior knowledge of the template sequences and is applicable to the preparation of templates from complex samples such as whole genomes or mixtures of cDNAs, as well as mono-template applications.

Although the above method works well, the present inventors have discovered that when sequencing or cloning nucleic acid fragments produced from amplified nucleic acid sequences, the ends of the amplified nucleic acid sequences are over-represented in comparison to those sequences internal to the ends of the amplified nucleic acid sequences (i.e., central or core sequences).

Not wishing to be bound by hypothesis, it is believed that accumulation of damage during fragmentation of nucleic acid sequences may affect or have greater affect on central or core sequences along the length of the original nucleic acid strand, as compared to those sequences at, or proximal, to either end. By way of an oversimplified example, if a nucleic acid strand 100 kbps in length was fragmented into 100 pieces 1 Kbps in length, the two pieces at either end of the strand would have one broken, fragmented end compared to those 98 central pieces derived from the middle of the strand which would have two fragmented ends. When the sample is processed and sequenced, the 'two' end fragments appear at a much higher frequency than the 98 'central' fragments. If the sequencing is performed on amplified isolated individual molecules, a large number of the amplified 'clones' or 'clusters' derive from the ends of the sample, meaning that the sequencing of, the central 98 pieces is less efficient due to the large over-representation of the two ends.

Without being limited to the hypothesis, the present inventors believe that when the end of the nucleic acid is derived from a synthetic oligonucleotide primer, the end of the strand is always a clean, blunt ended duplex that works very efficiently for ligation. However, when the end of the nucleic acid is derived from a random shearing process and enzymatic polishing, the end is less chemically clean, and therefore less efficient in subsequent ligation reactions. Thus it is likely that the efficiency of end-repair will also be lower for fragments that have two ends to be repaired rather than one. It is also likely that damage within each fragment could also affect the efficiency of amplification in downstream steps, and thus the fragments derived from the central region of the fragmented sample contain two polished ends, whereas the fragments from the end region contain one synthetic end and one polished end.

Thus such over-representation gives rise to a bias leading effectively to redundancy in both sequencing and cloning steps. The present invention addresses this previously unrealized problem by providing an improved method which reduces or removes over-representation of end sequences in a nucleic acid 5' and 3' modified library, and thereby is an improvement on the original method wherein the starting nucleic acid sample is a PCR product or other amplicon or other blunt ended duplex.

The term "5' and 3' modified library" refers to a collection or plurality of template molecules which share common sequences at their 5' ends and common sequences at their 3' ends. Use of the term "5' and 3' modified library" to refer to a collection or plurality of template molecules should not be taken to imply that the templates making up the 5' and 3' modified library are derived from a particular source, or that the "5' and 3' modified library" has a particular composition. By way of example, use of the term "5' and 3' modified library" should not be taken to imply that the individual templates within the 5' and 3' modified library must be of different nucleotide sequence or that the templates be related in terms of sequence and/or source.

In its various embodiments the invention encompasses formation of so-called "monotemplate" libraries, which comprise multiple copies of a single template molecule, each having common sequences at their, 5' ends and their 3' ends, as well as "complex" libraries wherein many, if not all, of the individual template molecules comprise different target sequences (as defined below), although all share common sequences at their 5' ends and 3' ends. Such complex template libraries may be prepared using the method of the invention starting from a complex mixture of target polynucleotides such as (but not limited to) random genomic DNA fragments, cDNA libraries etc. The invention also extends to "complex" libraries formed by mixing together several individual "monotemplate" libraries, each of which has been prepared separately using the method of the invention starting from a single type of target molecule (i.e. a monotemplate). In particular embodiments more than 50%, or more than 60%, or more than 70%, or more than 80%, or more than 90%, or more than 95% of the individual polynucleotide templates in a complex 5' and 3' modified library may comprise different target sequences, although all templates in a given 5' and 3' modified library will share common sequence at their 5' ends and common sequence at their 3' ends.

Use of the term "common" is interpreted as meaning common to all templates in the 5' and 3' modified library. As explained in further detail below, all templates within the 5' and 3' modified library will contain regions of common sequence at their 5' and 3' ends, wherein the common sequence at the 5' end of each individual template in the 5' and 3' modified library is not identical and not fully complementary to the common sequence at the 3' end of said template.

Use of the term "template" to refer to individual polynucleotide molecules in the 5' and 3' modified library indicates that one or both strands of the polynucleotides in the 5' and 3' modified library are capable of acting as templates for template-dependent nucleic acid polymerisation catalysed by a polymerase. Use of this term should not be taken as limiting the scope of the invention to libraries of polynucleotides which are actually used as templates in a subsequent enzyme-catalysed polymerisation reaction.

The term target is used to signify a fragmented polynucleotide of substantially unknown sequence. 'Targets' that are modified with known ends become 'templates' suitable for amplification.

Use of the term "ends" is a general term interpreted as referring to regions of sequence at (or proximal to) either end of a nucleic acid sequence. For example when referring to single stranded nucleic acid molecules the term refers to the 3' and/or 5' "ends". The length of the "ends" may be defined by the length of a synthetic oligonucleotide sequence, or may be derived from the length of the average length of the fragments. If the average length of the fragments in a fragmented sample is 100-200 base pairs, the length of the 'end' fragments will also be 100-200 base pairs. In a duplex where two complementary single stranded nucleic acid molecules are base paired then such a duplex will comprise two "ends" each with a 3' end from one single stranded nucleotide sequence and a 5' end from the other of the single stranded nucleotide sequences.

The term "over-representation" is used to refer to the case where the relative amount of a particular sequence, for example within a 5' and 3' modified library, is increased in comparison to other sequences within the 5' and 3' modified library. In a 5' and 3' modified library for example, it is desirable that the relative level of any one sequence when compared to the relative level of any other sequence in the 5' and 3' modified library is in an approximately equal ratio of 1:1. In an embodiment wherein the target polynucleotide molecules are random segments (fragments) of the primary polynucleotide sequence, if the 5' and 3' modified library covers the primary polynucleotide sequence to a depth 'd', then the average number of template polynucleotide molecules covering any point in the primary polynucleotide sequence should also be 'd'. Hence the composition of template polynucleotide molecules proportionally reflects the overall composition of the primary polynucleotide molecules. In context preventing over-representation therefore refers to the process of maintaining the relative abundance of particular nucleic acid sequences in a sample or 5' and 3' modified library such that there is uniform coverage of any point in the primary polynucleotide sequence by approximately equal numbers of template polynucleotide molecules.

In a first step modified primary polynucleotide molecules are prepared by adding a modification to the 5'-ends of the primary polynucleotide molecules.

In a particular embodiment the primary polynucleotide molecules may originate in double-stranded DNA form (e.g. genomic DNA fragments, PCR and amplification products and the like) or may have originated in single-stranded form, as DNA or RNA, and been converted to dsDNA form. By way of example, mRNA molecules may be copied into double-stranded cDNAs suitable for use in the method of the invention using standard techniques well known in the art. The precise sequence of the primary polynucleotide molecules is generally not material to the invention, and may be known or unknown. In a particular embodiment, the primary polynucleotide molecules are DNA molecules. More particularly, the sequence of the primary polynucleotide molecules is not known. Yet more particularly, the DNA molecules are PCR products. The primary polynucleotide molecules can be a biological sample of nucleic acids. The modified primary polynucleotides can be PCR amplicons from said sample, wherein said amplicons are obtained using primers containing a modification at the 5'-terminus, thus the 'modified' primary nucleic acids may only be a small fraction of the original primary sample, for example a 'modified' 5000 base pair fragment from a whole genomic 'primary' sample.

The sequence of the modified polynucleotide molecules may be the same or different for example, a mixture of modified primary polynucleotide molecules of different sequence may be prepared by mixing a number, greater than one, of individual modified primary polynucleotide molecules.

If the primary polynucleotide molecules are a mixture of short polynucleotide molecules such as DNA or products of around 500-1000 base pairs in length then it may be desirable to prepare a concatemer by ligating the primary polynucleotide molecules together prior to modification of the ends. In such instances the sequence at the terminus of each primary sequence may be unknown, meaning the primary sequence can not be modified using a PCR reaction. The ends of the duplex may however be modified by treatment with a modified nucleotide triphosphate, for example a dideoxynucleotide triphosphate and a nucleotide polymerase or terminal transferase. Thus the ends of the primary polynucleotides may be modified directly prior to fragmentation. The ends of the duplex may also be treated with a further duplex adaptor sequence that prevents amplification of the fragment after the ligation step, for example an abasic primer sequence.

Such modifications could be by a number of means provided that such modifications preclude adaptor ligation and/or copying in a primer extension reaction in later steps of the method. Such modifications are well known in the art and could include by way of non-limiting examples incorporating, by ligation, modified DNA molecules including non-natural nucleotides and/or non-natural backbone linkages, adding chemical modifications (for e.g. biotin) or using a 5'-3' exonuclease to generate incompatible overhanging ends, enzymatic processes or use of terminal transferase.

It could also be envisaged that the modified primary polynucleotide molecules could be produced by amplification of the primary polynucleotide molecules. In this case amplification primers could be utilised which contain modified DNA molecules including non-natural nucleotides and/or non-natural backbone linkages or chemical modifications such as biotin. On amplification of the primary polynucleotide molecules the modifications would be incorporated into the modified primary polynucleotide molecules to prevent, adaptor ligation and/or copying in a primer extension reaction. For example 5'-amino or 5'-biotinylated primers could be utilised during amplification of the primary polynucleotide molecules. The amplification primers could contain modifications such as abasic sites that prevent the polymerase copying to the absolute ends of the primers. The primers thus contain a 5'-overhang that prevents ligation to the 5'-end of the duplex. The amplified products (modified primary polynucleotide molecules) will subsequently comprise the modifications introduced by way of modified amplification primers.

In a particular procedure, the modified primary polynucleotide molecules are fragmented into small fragments (target polynucleotide duplexes), more particularly less than 1000 base pairs in length, even more particularly less than 200 base pairs in length. Fragmentation to a size of less than 50 base pairs is achievable, but not desirable as this is less than the read length of the sequencing reaction. An ideal fragment size is distributed around 100-200 base pairs. Fragmentation of DNA may be achieved by a number of methods including: enzymatic digestion, chemical cleavage, sonication, nebulisation, or hydroshearing, preferably nebulisation.

It will be appreciated by one skilled in the art that not all of the target polynucleotide duplexes produced by this method will contain modifications; generally only those fragments containing sequences from the ends of the modified primary polynucleotide molecules will comprise modifications. As a result of these modifications it is intended that such fragments either will not ligate or are effectively removed from later PCR amplifications by virtue of a failure to amplify.

Preferably the target polynucleotide duplexes will be made blunt-ended by a number of methods known to those skilled in the art. In a particular method, the ends of the fragmented DNA are end repaired with T4 DNA polymerase and Klenow polymerase, a procedure well known to those skilled in the art, and then phosphorylated with a polynucleotide kinase enzyme. A single 'A' deoxynucleotide can be added to both 3' ends of the DNA molecules using Taq polymerase enzyme, producing a one-base 3' overhang that is complementary to a one-base 3"T' overhang on the double-stranded end of the ligation adapter.

In a next step, adaptor polynucleotides are ligated to both ends of the target polynucleotide duplexes to form one or more adaptor-target constructs.

In one embodiment a ligation reaction between an adapter and the target polynucleotide duplexes is performed using a suitable ligase enzyme (e.g. T4 DNA ligase), which joins two copies of the adapter to each target polynucleotide duplexes, one at either end, to form adapter-target constructs. Those target polynucleotide duplexes which comprise modifications will be prevented from ligating to adaptors. The ligated products of this reaction can be purified from unligated adapter by a number of means, including size-inclusion chromatography, preferably by electrophoresis through an agarose gel slab followed by excision of a portion of the agarose that contains the DNA greater in size that the size of the adapter.

After the excess adapter has been removed, unligated target polynucleotide duplexes comprising modifications remain, in addition to ligated adapter-target constructs. The unligated target polynucleotide duplexes may be removed for example by selectively capturing only those target DNA molecules that have adapter attached, followed by washing or by other methods well known in the art. In this manner, end sequences which would previously have been over-represented in a 5' and 3' modified library are removed.

In an alternative embodiment, two copies of the adapter are joined to each target polynucleotide duplexes (including those comprising modifications), one at either end, to form adapter-target constructs. In this instance the modification is intended to prevent amplification of adapter-target constructs comprising modification, in 'downstream' steps of the method. As before, the products of this reaction can be purified from unligated adapter by a number of means, including size-inclusion chromatography, preferably by electrophoresis through an agarose gel slab followed by excision of a portion of the agarose that contains the DNA greater in size that the size of the adapter.

In a next step, a primer extension reaction is performed in which a primer oligonucleotide is annealed to an adaptor portion of each of the adapter-target constructs and extended by sequential addition of nucleotides to form extension products complementary to at least one strand of each of the adapter-target constructs wherein the extension products and optionally amplification products derived therefrom have common sequences at their 5' ends and common sequences at their 3' ends.

As mentioned, in a particular embodiment adapter-target constructs comprising modifications are not efficiently amplified for example, by way of non-limiting example, due to the presence of modified abasic nucleotides. Thus the number of adapter-target constructs comprising modifications are effectively reduced or removed from the 5' and 3' modified library.

The precise nucleotide sequences of the common regions of the template molecules in the 5' and 3' modified library are generally not material to the invention and may be selected by the user. In a particular embodiment the common sequences must at least comprise "primer-binding" sequences which enable specific annealing of amplification primers when the templates are in use in a solid-phase amplification reaction. The primer-binding sequences are thus determined by the sequence of the primers to be ultimately used for solid-phase amplification. The sequence of these primers in turn is advantageously selected to avoid or minimise binding of the primers to the target portions of the templates within the 5' and 3' modified library under the conditions of the amplification reaction, but is otherwise not particularly limited. By way of example, if the target portions of the templates are derived from human genomic DNA, then the sequences of the primers to be used in solid phase amplification should ideally be selected to minimise non-specific binding to any human genomic sequence.

Thus, preventing ligation of adapters to the target polynucleotide duplexes prevents amplification of target polynucleotide sequences derived from the ends of the primary polynucleotide molecules and as a result these sequences are reduced or removed from the 5' and 3' modified library. Directly interfering with amplification of the adapter-target constructs derived from the ends of the primary polynucleotide molecules also reduces or completely removes such sequences from the 5' and 3' modified library.

In yet another embodiment, a small amount of unmodified primary polynucleotide molecules can be added to the modified primary polynucleotide molecules prior to fragmentation. In this way 'adding back' a very small proportion of end sequences ensures that end sequences are represented within the finalised 5' and 3' modified library and are not completely removed. In still yet another embodiment, when the modified primary polynucleotide molecules are prepared by amplification, oligonucleotide primers could be used which anneal to sequences outside of the desired amplification product. In this instance a larger amplification product is generated which has sequences at either end not required for 5' and 3' modified library preparation. When processed according to the present invention loss of this additional sequence does not matter.

Use of the Template 5' and 3' Modified Library

Template libraries prepared according to the method of the invention may be used in essentially any method of nucleic acid analysis which requires further amplification of the templates and/or sequencing of the templates or amplification products thereof. Exemplary uses of the template libraries include, but are not limited to, providing templates for bridging amplification, surface amplification, solid-phase PCR amplification (of either monotemplate or complex template libraries). A particular use is in solid-phase PCR amplification carried out on a solid-support.

Whole-Genome Amplification

Template libraries prepared according to the method of the invention starting from a complex mixture of genomic DNA fragments representing a whole or substantially whole genome provide suitable templates for so-called "whole-genome" amplification. The term "whole-genome amplification" refers to a nucleic acid amplification reaction (e.g. PCR) in which the template to be amplified comprises a complex mixture of nucleic acid fragments representative of a whole (or substantially whole genome)

Solid-Phase Amplification

Once formed, the 5' and 3' modified library of templates prepared according to the methods described above can be used for solid-phase nucleic acid amplification.

Thus, in further aspects the invention provides a method of solid-phase nucleic acid amplification of template polynucleotide molecules which comprises: preparing a 5' and 3' modified library of template polynucleotide molecules which have common sequences at their 5' and 3' ends using a method according to the first aspect of the invention described herein and carrying out a solid-phase nucleic acid amplification reaction wherein said template polynucleotide molecules are amplified.

The term "solid-phase amplification" as used herein refers to any nucleic acid amplification reaction carried out on or in association with a solid support, such as a bead or planar surface, such that all or a portion of the amplified products are immobilised on the solid support as they are formed. In particular, the term encompasses solid-phase polymerase chain reaction (solid-phase PCR), which is a reaction analogous to standard solution phase PCR, except that one or both of the forward and reverse amplification primers is/are immobilised on the solid support.

Although the invention encompasses "solid-phase" amplification methods in which only one amplification primer is immobilised (the other primer usually being present in free solution), it is preferred for the solid support to be provided with both the forward and the reverse primers immobilised. In practice, there will be a "plurality" of identical forward primers and/or a "plurality" of identical reverse primers immobilised on the solid support, since the amplification process requires an excess of primers to sustain amplification. References herein to forward and reverse primers are to be interpreted accordingly as encompassing a "plurality" of such primers unless the context indicates otherwise.

As will be appreciated by the skilled reader, any given amplification reaction requires at least one type of forward primer and at least one type of reverse primer specific for the template to be amplified. However, in certain embodiments the forward and reverse primers may comprise template-specific portions of identical sequence, and may have entirely identical nucleotide sequence and structure (including any non-nucleotide modifications). In other words, it is possible to carry out solid-phase amplification using only one type of primer, and such single-primer methods are encompassed within the scope of the invention. Other embodiments may use forward and reverse primers which contain identical template-specific sequences but which differ in some other structural features. For example one type of primer may contain a non-nucleotide modification which is not present in the other.

In other embodiments of the invention the forward and reverse primers may contain template-specific portions of different sequence.

In all embodiments of the invention, amplification primers for solid-phase amplification are preferably immobilised by covalent attachment to the solid support at or near the 5' end of the primer, leaving the template-specific portion of the primer free for annealing to its cognate template and the 3' hydroxyl group free for primer extension. Any suitable covalent attachment means known in the art may be used for this purpose. The chosen attachment chemistry will depend on the nature of the solid support, and any derivatisation or functionalisation applied to it. The primer itself may include a moiety, which may be a non-nucleotide chemical modification, to facilitate attachment. In a particular embodiment the primer may include a sulphur-containing nucleophile, such as phosphorothioate or thiophosphate, at the 5' end. In the case of solid-supported polyacrylamide hydrogels (as described below), this nucleophile will bind to a bromoacetamide group present in the hydrogel. A particular means of attaching primers and templates to a solid support is via 5' phosphorothioate attachment to a hydrogel comprised of polymerised acrylamide and N-(5-bromoacetamidylpentyl) acrylamide (BRAPA).

The 5' and 3' modified library of templates prepared according to the first aspect of the invention can be used to prepare clustered arrays of nucleic acid colonies, analogous to those described in WO 00/18957 and WO 98/44151, by solid-phase amplification. The terms "cluster" and "colony" are used interchangeably herein to refer to a discrete site on a solid support comprised of a plurality of identical immobilised nucleic acid strands and a plurality of identical immobilised complementary nucleic acid strands. The term "clustered array" refers to an array formed from such clusters or colonies. In this context the term "array" is not to be understood as requiring an ordered arrangement of clusters.

Use in Sequencing/Methods of Sequencing

The invention also encompasses methods of sequencing amplified nucleic acids generated by solid-phase amplification. Thus, the invention provides a method of nucleic acid sequencing comprising amplifying a 5' and 3' modified library of nucleic acid templates using whole genome or solid-phase amplification as described above and carrying out a nucleic acid sequencing reaction to determine the sequence of the whole or a part of at least one amplified nucleic acid strand produced in the whole genome or solid-phase amplification reaction.

Sequencing can be carried out using any suitable "sequencing-by-synthesis" technique, wherein nucleotides are added successively to a free 3' hydroxyl group, resulting in synthesis of a polynucleotide chain in the 5' to 3' direction. The nature of the nucleotide added is preferably determined after each nucleotide addition.

The initiation point for the sequencing reaction may be provided by annealing of a sequencing primer to a product of the whole genome or solid-phase amplification reaction. In this connection, one or both of the adapters added during formation of the template 5' and 3' modified library may include a nucleotide sequence which permits annealing of a sequencing primer to amplified products derived by whole genome or solid-phase amplification of the template 5' and 3' modified library.

The products of solid-phase amplification reactions wherein both forward and reverse amplification primers are covalently immobilised on the solid surface are so-called "bridged" structures formed by annealing of pairs of immobilised polynucleotide strands and immobilised complementary strands, both strands being attached to the solid support at the 5' end. Arrays comprised of such bridged structures provide inefficient templates for nucleic acid sequencing, since hybridisation of a conventional sequencing primer to one of the immobilised strands is not favoured compared to annealing of this strand to its immobilised complementary strand under standard conditions for hybridisation.

In order to provide more suitable templates for nucleic acid sequencing it is advantageous to remove substantially all or at least a portion of one of the immobilised strands in the "bridged" structure in order to generate a template which is at least partially single-stranded. The portion of the template which is single-stranded will thus be available for hybridisation to a sequencing primer. The process of removing all or a portion of one immobilised strand in a "bridged" double-stranded nucleic acid structure may be referred to herein as "linearisation".

Bridged template structures may be linearised by cleavage of one or both strands with a restriction endonuclease or by cleavage of one strand with a nicking endonuclease. Other methods of cleavage can be used as an alternative to restriction enzymes or nicking enzymes, including inter alia chemical cleavage (e.g. cleavage of a diol linkage with periodate), cleavage of abasic sites by cleavage with endonuclease, or by exposure to heat or alkali, cleavage of ribonucleotides incorporated into amplification products otherwise comprised of deoxyribonucleotides, photochemical cleavage or cleavage of a peptide linker.

It will be appreciated that a linearization step may not be essential if the solid-phase amplification reaction is performed with only one primer covalently immobilised and the other in free solution.

In order to generate a linearised template suitable for sequencing it is necessary to remove the complementary strands in the bridged structure formed by amplification so as to leave behind a linearised template for sequencing which is fully or partially single stranded. Most preferably one strand of the bridged structure is substantially or completely removed.

Following the cleavage step, regardless of the method used for cleavage, the product of the cleavage reaction may be subjected to denaturing conditions in order to remove the portion(s) of the cleaved strand(s) that are not attached to the solid support. Suitable denaturing conditions, such as hydroxide, formamide or heat will be apparent to the skilled reader with reference to standard molecular biology protocols (Sambrook et al., 2001, *Molecular Cloning, A Laboratory Manual,* 3rd Ed, Cold Spring Harbor Laboratory Press, Cold Spring Harbor Laboratory Press, NY; Current Protocols, eds Ausubel et al.).

Denaturation results in the production of a sequencing template which is partially or substantially single-stranded. A sequencing reaction may then be initiated by hybridisation of a sequencing primer to the single-stranded portion of the template.

Thus, the invention encompasses methods wherein the nucleic acid sequencing reaction comprises hybridising a sequencing primer to a single-stranded region of a linearised amplification product, sequentially incorporating one or more nucleotides or oligonucleotide cassettes into a polynucleotide strand complementary to the region of amplified template strand to be sequenced, identifying the base present in one or more of the incorporated (oligo)nucleotide(s) and thereby determining the sequence of a region of the template strand.

One particular sequencing method which can be used in accordance with the invention relies on the use of modified nucleotides that can act as chain terminators. Once the modified nucleotide has been incorporated into the growing polynucleotide chain complementary to the region of the template being sequenced there is no free 3'-OH group available to direct further sequence extension and therefore the polymerase can not add further nucleotides. Once the nature of the base incorporated into the growing chain has been determined, the 3' block may be removed to allow addition of the next successive nucleotide. By ordering the products derived using these modified nucleotides it is possible to deduce the DNA sequence of the DNA template. Such reactions can be done in a single experiment if each of the modified nucleotides has attached thereto a different label, known to correspond to the particular base, to facilitate discrimination between the bases added at each incorporation step. Alternatively, a separate reaction may be carried out containing each of the modified nucleotides separately.

The modified nucleotides may carry a label to facilitate their detection. Preferably this is a fluorescent label. Each nucleotide type may carry a different fluorescent label. However the detectable label need not be a fluorescent label. Any label can be used which allows the detection of an incorporated nucleotide.

One method for detecting fluorescently labelled nucleotides comprises using laser light of a wavelength specific for the labelled nucleotides, or the use of other suitable sources of illumination. The fluorescence from the label on the nucleotide may be detected by a CCD camera or other suitable detection means.

The invention is not intended to be limited to use of the sequencing method outlined above, as essentially any sequencing methodology which relies on successive incorporation of nucleotides or oligonucleotides into a polynucleotide chain can be used. Suitable alternative techniques include, for example, Pyrosequencing™, FISSEQ (fluorescent in situ sequencing), MPSS (massively parallel signature sequencing) and sequencing by ligation-based methods.

The target polynucleotide to be sequenced using the method of the invention may be any polynucleotide that it is desired to sequence. Using the template 5' and 3' modified library preparation method described in detail herein it is possible to prepare template libraries starting from essentially any double or single-stranded target polynucleotide of known, unknown or partially known sequence. With the use of clustered arrays prepared by solid-phase amplification it is possible to sequence multiple targets of the same or different sequence in parallel.

The invention will be further understood with reference to the following non-limiting experimental example:

Example

Experimental Overview

Long range PCR was performed on a BAC vector (bcX98521) containing a human genomic insert using two sets of primers

```
Set 1:
                                          (SEQ ID NO: 1)
    5' CGAGGAACTCAGCACTCATC (SEQ ID NO: 2)
    5' ATGCCGAGGAAGAAGCCATT

Set 2
                                          (SEQ ID NO: 3)
    5' TTTnTGGAACAGCCGCTCTCACCT (SEQ ID NO: 4)
    5' CCCnTCCTGGAGGGAAGTGACTAT
```

Set 2 primers have an abasic nucleotide at position 'n' in their sequence.

The resultant PCR product from primer set 1 is as follows:

```
                                                        (SEQ ID NO: 5)
CGAGGAACTCAGCACTCATCCTCACCCAGCAGGGCATAAGGGTTTCGGCCAGCCAGGCTG

GACCCTGGAGCCGAGGTTGGGGTCTCCTCATCCCCTTCTCCCTCCTCATCCGCATCCCGG

TCCTCCTCTCCCTCCTCCTCACAGGAGCTGCTCAGCTCTTCCTCTTCCTCCTCCTCCTCG

TCACCTGCTGGCCCCACCCTGCCCTGCAAAACCACCAGCTCCGTGGTCTCTGGATGGGAC
```

-continued

```
TCCCAGGTGCCTGGGGAACCAAAACAAGAAAAAAATGGAGGAGAGTTTTGAGCAAGAACT

AAAGCCAAGGAAAGATGGGGAAGAGGCAAAGACTAGGAATAACAATAATCTTTAGAGCTG

CTGGCATTCATTCATTCATCCATTCATTCAACTTCCTATGTGCAGATTGCTGAACAGAAC

CTTTGTGCACATCAACTTCAATCTTTACAATCACTATGCTAAGGGTCAATTATTACCCTC

AGTTTGCAGATCAGGAAAATATCACAGATGTTAAGTAACAGAGCTAGCCAACAGGTACAG

AATCCAGGTTTGACCCTCTCTCTGGCCACAAAGCCCACACCCTTTTACCTACGCTATAGC

AGGGGGCTGGGGAAGAATATCTGGGCTCTGACCTTTCTGTTCACTGTAGCCTGGGGATG

AAAACACAGGCTGAGGCGGCCGTCCACTGCCAGCCGCAAGAGACTGTTGGCTGCTCTGTA

CACATCATTCCGAGCCGCCTTGGCTGTCTTGTAACCACGTTTCTCTGCCCAGGCTGGAGG

AAGAAAAGAATAATGGAAAGGGAAAGCATTAACCAGGTACCAGTTATACTCCCACTCCCA

TAACACAGTCCTTCCAGTTTTCCCCAAAACATTCCAGGCCAGAGATCTTACTGGCTATGC

AACAAAAATCTAGGGGTGAGTGGACAGCAGCTTCATCAATGGCAGAATCTCTGAGGAGAG

GAAAGGAGACAGGGAAGGGTAAAAGGCGAGGCAGGTAAGGAAGAGCAGCTGAAACCAGGT

GGGGCGAAGCCAGGCACATGGAACTCACCTTCACAGATGTCCCAGGCACACCAGGGGTGT

TCCGCTGAGGGGTCCTCAGCCTCTGGGTGGCGCAGGTGGAGCAGGGCCTGCACGGGAATT

CGGGAGGCCAGGTAGCCCACAGCAGTGTAGGGCTCCTGGATCTGGGCGATAGGGTAGATC

CCCGCCAGAACCTGAGGGAAATGAGCACTCAGTACTTTCCTCAATGTCCCACCTTCTCTC

TTTCCCTTACCCACCCTCCCCGTCATACCTGCAACTGCCTAGGCAGAAGAGATGGGAAGA

TGAGGCCTGGGCAGTCACAGAGCTTCACAGAGGGGGTAAGAAAGTAGGTCTGAAAGTATC

GGGTATGGCCCGGGGTTCTGGAGACACTCACGACTTTCCGCCCCACCAGCCCATTGATCA

GCGAGGACTTTCCCACATTAGGGAAACCTGAGGAAGGCAAGGAAAATTAACGTTTAACAG

GTTTCTACTCTGTGATGGGACTTGGTGCTATACCTATAGGTAAAAGGGGAACTAAGGCTC

AGAAATTAAGGAAATGGTATTGCAGAATACAAATCACGCTCTGGGCTGCCAGGGTTAAAT

CCTGGCCCTTCCACTTACCAGCTTTGTGATGTCAGGGCAACTAACTTTCTGAGCCTCTGT

TTCTTCATTTTACAGTGTGGACACCTCCCTACCTCAGGGTGGTCAGGATTAAATGAGATA

ACCAATACAACTTGTGTGGGTCAGTGCCTGCAGTACAGTAAGTACCCAGTACCAGTGATC

CACATCTCATAATTACTATGACTTGGCCTGGoACAGTGGCTCACGCTTGTAATCCCAGCG

TGATTACTTTGGGAGGCCAAGGCGGGTGGATCACCTGAGGTCAGGACTTCAAGACCAGCC

TGGCCAACATGGTGAAACCCCATCTCTACTAAAAATACAAAAATTAGCTGGGCGTGGTGG

TGGGCGCCTGTAATTGCAGCTACTTGGGAGGCTGAGGCAGGAGAACCACTTGAACCCAGG

AGGCGGAGGTTGCAGTGAGCTGAGATTGCACCATTGCACTCCAGCCTGGGCAATAAGAGG

GAAACTCCATCTCAAAAAATAATAATAATAATTACGATGACTTGTCCAAGGAGAAAACTG

GAAGCCTTGGGGCTCACTGCCACTCTGCTCACTCACCACCACCAGTTTTTGTGTTTCTGG

CTGACTTCAGTGCCTTCATCTCCCTTCCACAGAGCATCTCCTTTACCCCACCTCAGCTGC

CCACTCCCATGGTAATACCTGCATCTTGTCACTTCACAGCTCCAAAGCCTCAATTCCAAG

CACCCCTCTCTGCCCTGACAACTCATCTTTCCAGCTCACTTACTCTGGTTACTCCATGCC

AGTAAGTCTTTGACCCCTGACCTTAACACAGTAACACTATGCAATACCCAACTCGTGTCC

TCAATTTCCTTCTTACTTGACTCAGATTTCATGATCCAGCTCCTCAGCCAGGGCCGTTCA

CAGACCTGGAACTCCCTGGTCCCACTTCTCCCCTCTATCTTACTCACCTGGCAAAATCCC

AACCCTGTAAAATCCAGCTCTGCCCATTCAGCACTGCTCCTGGGCAGCTGACTGTGGCTA

AGAAAAGATGTACCACTGTGCTCACTCTTTACAACACATGCAAGTATCTAGGAGGAAGGG
```

-continued

```
AGGGAAGGAGGGAGAAAAAAGTTCTCCTTTGACGACCACCACCAGACCTAGTTCTCTGTC

CGCTTTGCAGGAAAACTCCTTAAAAGACTTACCTACTTTTTTCACCATTTCTTCCTGCTA

TCTTCTTTGTAACTGTAAACTACAACATACAAAAAAATGCACAGAACATACATGTGCAGC

CTGATGAACCCCATACCACCCAATGTGTGACAACATGTTCCATCTGTCCTTGTTTTTTTT

TGTTTTTGTTTTTGAGACAGAGTCTCACTCCCTCACCCGGGCTGGAGTGCAGTGGTGCGA

TGTTGGCTCACTACAACCTCATCCTCCCAGGTTCAAGCGATTCTCGTGCCTCAACCTCCT

GAGTAGCTGAGACCACAGGCGTGCGGCTCCACACCTGGCTAACTTTTTGTATTTTTAGTA

GAGATAGGGTTTTGCCATGTTGGCCAGGCTGGTCTCAAACTCCTGACCTCAAGTAATGCG

CCTGCCTCAGCCTCCCAAAGTGCTAGGATTACAGGGATGAGCCACCATACCGGCCGCCAC

TCATCCTTCTTGATCATAATCCTCTCCCTCTATACATGCAAGCTTTATCCTTTTAAGGAA

ATCAACTCCTTACATTTCTCTTTAGTTTATGACCTGTGTATCTCTCAACAATGCAGCTTA

ATTTTGCAGCTTTCAAACTTGATAGAACTGAAATTGTGCAGTATGGATGCTATTGGGTCA

GACTCTTTTCACACAATGTTATGTGAAGTTGTTGCACCTTCTCTCATGGGCCTACTCCAG

TTTGGCTTTCTCCACCCCACTGAAACCACGGATCTTCACATTGCCAAGCCTGCTGAGCAG

CTCTCTGTTCTCTCATTTGGCCTGTCAGCAACAGTTGACACAGCTGATTCCTCCTTTCCT

CTTCAAACACCTTCTTCATTTGACTTCTGGGACGCTCCCTTGGTTTTCCTCCTTCTCACT

GTCCTTTGCCCAACTAAATGCTGGCTTGTCCTAAGGCTCAGTCCTTGACCTCCTCTTCTC

CAACTATTTCCTTTCTCTCCTACATCTCATCCAATTCCATGGCTTTTTTTTTTTTTTTT

TGACGAAGTCTTGCTCTGTCACCCAGGCTGGAGTGCAGTGGTATGATCTTGGCTCACCGT

AACCTCCGCCTCCAGGATTCAAGCAATTCTCCTGCCTCACCCTCCTGAGTATCTGGGACT

ACAGGCACGCACCACCACACACGGCTAATTTTCTGTATTTTTTGGTAGAGACAGGGTTTC

ACCATGTTGGCCAGGCTGGTCTCAAACTCCTGGCCTCAAGTGATCCACCTGCCTCAGCCT

CCCAAAGGGCTGGGATTATAGGCATGAGCCACTGTGCCCAGCCTAATCCTGTGGCTTTAA

ATACCACTTATATCCATCAATGGTTCCCCAAATTTAAATCTTTCCCAAATTCAAATTTCC

GTCCTCTTCTCTCCCCTAAGCTGCTGACTACTTACCCACTGCCTATTCAACATCTCCACT

AGGGATATTTAAAAAGAATCTGAAATTTCATTTCTGATTCCCCTCTCCTCCCCAAAGCCT

TCAAATCTGCTTCTCCCCCAGTCTTCCCATCTCAGTATTTCCAGTTGCTCAAGACAAAAA

CCTGGAAGTCCTTCTTTATCCTCACTTTCCTTCACGTGCCAACTGCAAGCCATCAGCGAT

CTCATTTTCTCTACCTTCAAAATATATCATGCTTCCGGCCCTGTCTCACCACCTCCAGCT

CCAGCATCCTACTCTAAGCAACTCTTATTTCTCTCCTAGATTACTGAAATAGCCTCAACT

GCTCTCTCTGCTCCCTTTCTTGCCCACCCCCCATCATTTATTCTCTACTCAGGAGGTAAA

CTTATAAGAAACAAAATCAGATCCTATCATTCCCCTGTTCAAAACCTACCCTTGGCTTCT

CATGAGACTTGGAATAAAATCCAAAATGGCTGTCACAGCCTCAGGGCTCTACATGATGTG

GGCCCTGGTGATCTTGCTGACCTCATCCCCAGTACTTTATCCTGGCTCCCATACTCCAAT

CCCCTGGGCACTCTTGCTGGTCCTAGAATCTCCAAGCCCATTCCCTCCTCAAGACCCTTT

CCCCACAGTTCTGAATGGCTCACTTCATCTCATCATCCAGTTCTCTCCTCAGGGAGGTTT

TCCCTGAGCACCTCTCCTCTCAGTCACTCTCTATCCCCTTTCATTGCTTTATTGCCTTCA

CTGCCCCTACATGATTTCGGATCACAAAATCTATTTACTCACAAGAAAATAAGCTCCATG

AATCTACAGACCTTTTTGCCATTTCCACAGCAGTATGTCCCATCCCTAGAATATCTGGCA

CCTGGTTAAGTGTTCAGTACATATTTGTTGAATGGGTAAATGAATGAGAGCTGGAGGGAA
```

-continued
```
ATCCAAACTCAGGGGTGCCTGTGCCACAGCAAACACTCTCCCTCTCACACCACCTGGAAT
AGAGATCAGCTAGAGCAGAGGCTGCTAAGAGAGGGAACAGAGGCTCCTTGTGACAGGGAG
ACTAGGATCAGAAGTCAGGGAAGGGACAGCCGGGTGAAATGACTGGAAAGAGGAGCAATC
ACTCAGCAGTAAGGCAGGTTCTTCCAAAGACAAAAAGGACACAGAGATAAGTCAGGGCAC
TTCCAAGGAACCCAACTACCTACTCCACACTCCCAAATTTATTCTGGGTTGGGCCCTTTT
TGGTTCCAATATCACCTCGGATACCATAACTTGTCCAAGGTCTCTTCTTACCTCTCCCAC
CCTAAATGAAGACGGGCCCTGGGTCCTAATCATACATTCCTTTTTCCTCCACTGTGAGCT
GAGACAAAGCCCTTAAGAGGAGATTCTCCTTGGCAACAAACTTAAAGGOTTAAAACCTAG
AAGAATACTAATTCTTGCTGAGCTCCTACTATGATTTGATAATCACTGTACTACAGACTA
ATTACTACAATTCAAATGGTTTATATAAACCACTTAAAACAGTGCCTGTTACATAGTAAG
CACCATATAAATACTGAGTTTTAACAATAATAATTGTTATTATTGTTATCACTATTTGTC
AGGCATTCTTACACTCTCTTAACACTATTCCCATCATTCCTCACATCCATTCTTTTTTTT
TAAAGACAGGGTCTCTATCAGCCAGGCTGGAGTGCAGTGGCACAATCATAGCTCACTGCA
GCCTTGAACTCTTGGGCTCAAGTGATCCTCCTGCCTCAGCCTCTGAAGTAGCAGAGACTA
CAGGCACATACCACCACACTTGGCTAGTTTTCTTTATCTTTTGTAAAGATGGGGTTTCAC
TATGTTGCCCACACTAGTCTTGAGCTCCTGGTCTCAAGCAATCCTCCCACCTCAGCCTCC
CAAAGCGCTGGGACTATATAGGCATGAGCCCTCACACATGGCCGTCATCCATTCTTTTAC
TCAGGTATCAATGTCCTTATTTTTAAAATCAAAGTAACTAAGACTCAGAGTAGCAAAATC
ACTTACTCAAGACCTCACAGCTGAGAAGAGGTGGAATTTAACTCAGGCTGTCATGATCCT
TCCACTGCAGCAGACGCCTCTTCTGCCTTGCCCACCGCCACTGGCAGAGATCACCCCTCA
GACACCCTGGGGCCTAATGAGACCTGATCGCCCTCTCTCTTCTCCGAATATGAAAACTCT
GTACCTCCTTGGAGGCCACCACGCACAAGCTGCCACTTCCTTACCCACACAGCCGATGGT
CACCACCCCATCCTTGTAGCGCTCTTGGGTTGGGCCAGTTGGCTCCATTGCTGAATCAGT
CTGCTGCTCCACCAGGACTGCTGGGCCATCCTCCTCTTCCTCCTCCTCCCCAGAGCCATT
ACCCCAGGTGGCCCCAGCCACATCCCGAGCAATCTTCTCCCGCCAGCTGCTCAAGTCCAC
TGCTCAAAGAAGGAGAAGATTAAAGAGGTTCTCCCCAGGGCTGCTGTGCATGATGGCACA
TACTGTGCCCTGCACAGATTATGTAACTGGCACCCTCTGGAGTTGTACAGTGCCAACCTA
AATAAGAGCAGGTCAGAGAATCTCCCAAAAGTCATTTGACCCTACCCTCCCTGGAATCAC
GCACGTTTCTCTGAGCTTCTGAAAAGTACTGGGAAGGCTAAAGGCAGCAAGCCACTGAGG
CTCCTGACTACCTGCTGCCTCTCGTCCCACCAAGTCAGTCTGCTCCTTATTCTGTCCCTT
CCCCTGGCCTCTTGCACATATCCACCATAGAGGGGTTGGCTTCAGGAAAGGTGAGCAAAA
TGATTCTGCATCTTTGGTCTCCCCCATGTCCTCCTACAGCCCTCCTCTAAGGGCCACATA
CCTTTCCCCACAGTGATGGCTTCACAGGCTCTCAGCAACTGCTCTGGCCCCAGGGCCCGA
GTCCATCCTCTCCCCCGCCTCCGACTCTTCTTCAAGACTGAGATCAGAGGGCACAAAAGG
ATGGGCACACGGGCTTAGGCCTCTCATCTCTCCCACCACCCTTAGGCCCAAGACCAGGTG
CCCCCTTGTCAATAAGCCTCTCTGTTCTCCCCTTTGTCCCCTGCCAACTCACCTCTCCCA
AGTTGCCCTCTCTCATTGCCCACTCACCACTACTAGGATCCTGTGGGGTGCGGGGTCCC
GAGGAAAAGAGGTGAAAAGGACGACGTGGAGCTGGGGATAGTGTTGATGGAAATAATGCT
TCCAGGCAACCACAAGAGCTGGCGGGGCCAGATCCACCTTGTTCAAAACCAGCACCAGGG
CCAGTCCAAGTTCTCCAGTCACATACTCATAAAGTGCTGGCGGGAAATTCACAACCTAGG
ACAGAGTTGATAAGAGGATGGAGCAGTGAAAGTCAACCCAGAGTTCTCTGCCTCCAGCTC
```

-continued

```
CCCACTCAGCAGGTGTAGCTCAGAGACAAGGCCCTGGTGGTAGCAGACTCTGGGCTAAAA
ACTATAAACCAGACAAACTGAAAAACAAAGACAAAACAGGGGTTAGTAATACTTCTGAGT
CTCAGAGGGCTTCCTATAGGTCATGATTAGAGATGGAAATGAACCCAAAACAAGACAAGG
AAACAGCATCACTTAGCACACTGAGGTAAAGGCTGGGATCGGAAACAGGGATGGGGGTTA
GGGTAGAAATTAGTCTGCTTTTTTGTGTGTGCACAACTATGTAAGTGTGTACACGTGCAT
ATATGCATGCATGCAAGTACGTGCACATGTGTGCATGTTTGTGTGTTAATGTGACTGTGA
ACATGTGTGCAAACATGCCTGTGTATATTGATGTGCACATGATGTACGTGTGAGTATGTG
TGTGTACATATTATTAAGGACCTCCAACCTAAATGGTCCTCACAGACCTCCCTTTCTCCC
ACTGGAGGACAAGAGTGAAGTTGCAGAGCTAGGATTCACACAGGGCAGTCCAGCAGCAGT
CTACAGCCTTAACTACTACTCTAGCATTCCAGGTGGGTTCTGTAGCAACTGATGTGGCAG
TGCTAGAGAAATGAGATAAGGAAGAAAGGGCATCTTTGGGCTGGGCAGGAGGAAGTCCCC
AGCTGCATTCATAGAATCCCTGGAGCTCCAACACTTGGATTTTCTATTGGTCTGTGATGA
GCTAAAGGACAGGACATGGCTGTTTTGAAGAGAAGAGTGAGCTGGCCAAGGGAGGAATGA
CAGGCTATAAGAGAATAAAAAACTGAGTTCCTAACTGCGGACATCAGCACTAGGTAGAGA
TTAGAAAGACAGGAAGATAGATACCTCTCTGTCTCCCAACTCTTGCCTCTGACCTTTGCC
CCTGAAAAACCTTTCTCCCTCCTCCTTGCCCACCCTTATCCCTAGTACTCACTGGATGTC
GGATATCAGTGATAAGCAGGACGATGTCAGACATCTCTAACACCCGCCACAGCTGCCTCC
ATGTCTAAAAAGACAGGATCAGGAAGAGAAACTGAAAACAGAGTCCCTCTCCAGCCTGAT
CCCAAACCAATTTGACCATAGGTCACTATGCCCCACTCCTGTCCCTAGAGTACACTGTCA
CCTCCAGATTGTGCTCAAAGTAGCTGAGTTTCTCAGAGGAGTAAGCCCCATGAATCTTCC
CAAGATAGTCTTGGAAGCTCCGTTCCTCTTGGCTCATTAGTTGCTCCTTGGACATCTCAT
AGCTCCAAGGAGGACGTCGAGGAAAGTCCAGAACTGGGAATTCAGGAAAAAGTCCAAGTG
TGAGGAAATCTTCAGGATTCAAGAGTACATCCCAGACCCCTCCTTCCTCACAGTCGGCTT
TTACCTTTCCAAACTCCTTCCCCAGCCCAATGCCTGTCTTGCTCTCACTCACCTGAGCCA
GGCTGATACACCTCCCGGATGTCCAGCTCCAACAACTCAGCACTGACCGGCTGTAGAACT
TGCTCCCGGGCTGCTCTCTTTCTCCTCTCTACCTCCTCCCTGCTGTCTCTCTCAAAATGC
AGTCGGTATCTAAGGGAACAGGGACCGAGACATCCAGAGCAATCCTGTGCCACAAACTC
CTATTTTCTCCCCTCTTGTACAATCAACTTCGCAAACCATTCTCTCCAGAGTCGTTCAAG
TCTCCTCTCTCAAGTCAGACTTCCCCCAAGTCCTTCTTTCAGGCAATACTCAGCCTTCTC
CTTCTAAAAGCCCAACTCTCTCCAGCCCCTCTGGAAAGGAAGACTGTGGCCCGCTGTGGG
GAGCCGAGTGGCTAGCGGAGAACTGTGGCATCCCAGGCCCACCGTCTTCACCAGTAGCAG
CCCGCTTTCCCCCAAAGCTCTGACTTCCGGGTAGGCGGGAAAGCCGGGACCAGCGCCCCC
TCCCACCCTCACCGATTTGGGTCGTAGCCTCGTGGACCCAGCCCCTGAGAAGGCTGCTGG
TTAAGCCTGCGGATATGATGGGTCACAGACTCCCCGTCCGAGGTGTCGGTCTGTTCCTCT
CGCCGCTCCCGGCTCCCGCTGCGGCTGTTGGAACTGGAGCGCAGCCCATCTTGAAGCCCT
GCGGGGAGGGGCCGGTGACGCCAGTGCTGGCCAGCTCTCAGGGGCCATAAGACCCTCTCC
CCCATCGGCCTGACTCCCTTTCATCCCACTCAACTTCTTCCGATGTTCAGTCCTCCCAGA
CACCCTATTTGGGACCCTCCCGGATGTGCGTGGGGGAGTCACTCCTTCAGGGAGCAGTG
GGGACGCGCCCCGTGCTAGCTGGAGGGATTCCCCTCCCCCAACTCTCCATCCTTCCCCA
CCCCTTCCAGATGTAGGGGGGGTGGGGGATCCCCTCCGCGATAGGCCGCGAGGGTTGACG
```

-continued
CGGTCCCACGACCCCCTCCCACGATCCCCAGAGGTGCAGCGGGCACACCCCTCCTTCCAG

ATGTGCGGAAGCCCGAGCCCCGCCCCCTCCTCCCGCTCCCGCACTGACCTCTCTTCCGCT

CCCGTTTGTCCTGCAACTGCTTCTTCTTCTGCTTCACGCTGAATGGCTTCTTCCTCGGCA

T

The resultant PCR product from primer set 2 has 5' overhangs at both ends: one end comprising the overhanging sequence 5'TTTn, and the other end comprising the overhanging sequence 5'CCCn (where n is an abasic nucleoside). The double-stranded portion of the PCR product comprises the following sequence:

(SEQ ID NO: 6)
TGGAACAGCCGCTCTCACCTCAGTTCATCTGGGGAAGGGGCTACAAAGCAAACAATCTTT

ATTCACAATTGGGGTGGCAGAGGGGAGATACCCCCAGGTCAGTCCAAAAGCAAAGATACT

GGGAGGGAAGATGGCGCTGGGCGAGGAACTCAGCACTCATCCTCACCCAGCAGGGCATAA

GGGTTTCGGCCAGCCAGGCTGGACCCTGGAGCCGAGGTTGGGGTCTCCTCATCCCCTTCT

CCCTCCTCATCCGCATCCCGGTCCTCCTCTCCCTCCTCCTCACAGGAGCTGCTCAGCTCT

TCCTCTTCCTCCTCCTCCTCGTCACCTGCTGGCCCCACCCTGCCCTGCAAAACCACCAGC

TCCGTGGTCTCTGGATGGGACTCCCAGGTGCCTGGGGAACCAAAACAAGAAAAAAATGGA

GGAGAGTTTTGAGCAAGAACTAAAGCCAAGGAAAGATGGGGAAGAGGCAAAGACTAGGAA

TAACAATAATCTTTAGAGCTGCTGGCATTCATTCATTCATCCATTCATTCAACTTCCTAT

GTGCAGATTGCTGAACAGAACCTTTGTGCACATCAACTTCAATCTTTACAATCACTATGC

TAAGGGTCAATTATTACCCTCAGTTTGCAGATCAGGAAAATATCACAGATGTTAAGTAAC

AGAGCTAGCCAACAGGTACAGAATCCAGGTTTGACCCTCTCTCTGGCCACAAAGCCCACA

CCCTTTTACCTACGCTATAGCAGGGGGCTGGGGAAGAATATCTGGGCTCTGACCTTTCTG

TTCACTGTAGCCTGGGGGATGAAAACACAGGCTGAGGCGGCCGTCCACTGCCAGCCGCAA

GAGACTGTTGGCTGCTCTGTACACATCATTCCGAGCCGCCTTGGCTGTCTTGTAACCACG

TTTCTCTGCCCAGGCTGGAGGAAGAAAAGAATAATGGAAAGGGAAAGCATTAACCAGGTA

CCAGTTATACTCCCACTCCCATAACACAGTCCTTCCAGTTTTCCCCAAAACATTCCAGGC

CAGAGATCTTACTGGCTATGCAACAAAAATCTAGGGGTGAGTGGACAGCAGCTTCATCAA

TGGCAGAATCTCTGAGGAGAGGAAAGGAGACAGGGAAGGGTAAAAGGCGAGGCAGGTAAG

GAAGAGCAGCTGAAACCAGGTGGGGCGAAGCCAGGCACATGGAACTCACCTTCACAGATG

TCCCAGGCACACCAGGGGTGTTCCGCTGAGGGGTCCTCAGCCTCTGGGTGGCGCAGGTGG

AGCAGGGCCTGCACGGGAATTCGGGAGGCCAGGTAGCCCACAGCAGTGTAGGGCTCCTGG

ATCTGGGCGATAGGGTAGATCCCCGCCAGAACCTGAGGGAAATGAGCACTCAGTACTTTC

CTCAATGTCCCACCTTCTCTCTTTCCCTTACCCACCCTCCCCGTCATACCTGCAACTGCC

TAGGCAGAAGAGATGGGAAGATGAGGCCTGGGCAGTCACAGAGCTTCACAGAGGGGGTAA

GAAAGTAGGTCTGAAAGTATCGGGTATGGCCCGGGGTTCTGGAGACACTCACGACTTTCC

GCCCCACCAGCCCATTGATCAGCGAGGACTTTCCCACATTAGGGAAACCTGAGGAAGGCA

AGGAAAATTAACGTTTAACAGGTTTCTACTCTGTGATGGGACTTGGTGCTATACCTATAG

GTAAAAGGGGAACTAAGGCTCAGAAATTAAGGAAATGGTATTGCAGAATACAAATCACGC

TCTGGGCTGCCAGGGTTAAATCCTGGCCCTTCCACTTACCAGCTTTGTGATGTCAGGGCA

ACTAACTTTCTGAGCCTCTGTTTCTTCATTTTACAGTGTGGACACCTCCCTACCTCAGGG

TGGTCAGGATTAAATGAGATAACCAATACAACTTGTGTGGGTCAGTGCCTGCAGTACAGT

AAGTACCCAGTACCAGTGATCCACATCTCATAATTACTATGACTTGGCCTGGCACAGTGG

```
CTCACGCTTGTAATCCCAGCGTGATTACTTTGGGAGGCCAAGGCGGGTGGATCACCTGAG

GTCAGGACTTCAAGACCAGCCTGGCCAACATGGTGAAACCCCATCTCTACTAAAAATACA

AAAATTAGCTGGGCGTGGTGGTGGGCGCCTGTAATTGCAGCTACTTGGGAGGCTGAGGCA

GGAGAACCACTTGAACCCAGGAGGCGGAGGTTGCAGTGAGCTGAGATTGCACCATTGCAC

TCCAGCCTGGGCAATAAGAGGGAAACTCCATCTCAAAAAATAATAATAATAATTACGATG

ACTTGTCCAAGGAGAAAACTGGAAGCCTTGGGGCTCACTGCCACTCTGCTCACTCACCAC

CACCAGTTTTTGTGTTTCTGGCTGACTTCAGTGCCTTCATCTCCCTTCCACAGAGCATCT

CCTTTACCCCACCTCAGCTGCCCACTCCCATGGTAATACCTGCATCTTGTCACTTCACAG

CTCCAAAGCCTCAATTCCAAGCACCCCTCTCTGCCCTGACAACTCATCTTTCCAGCTCAC

TTACTCTGGTTACTCCATGCCAGTAAGTCTTTGACCCCTGACCTTAACACAGTAACACTA

TGCAATACCCAACTCGTGTCCTCAATTTCCTTCTTACTTGACTCAGATTTCATGATCCAG

CTCCTCAGCCAGGGCCGTTCACAGACCTGGAACTCCCTGGTCCCACTTCTCCCCTCTATC

TTACTCACCTGGCAAAATCCCAACCCTGTAAAATCCAGCTCTGCCCATTCAGCACTGCTC

CTGGGCAGCTGACTGTGGCTAAGAAAAGATGTACCACTGTGCTCACTCTTTACAACACAT

GCAAGTATCTAGGAGGAAGGGAGGGAAGGAGGGAGAAAAAAGTTCTCCTTTGACGACCAC

CACCAGACCTAGTTCTCTGTCCGCTTTGCAGGAAAACTCCTTAAAAGACTTACCTACTTT

TTTCACCATTTCTTCCTGCTATCTTCTTTGTAACTGTAAACTACAACATACAAAAAAATG

CACAGAACATACATGTGCAGCCTGATGAACCCCATACCACCCAATGTGTGACAACATGTT

CCATCTGTCCTTGTTTTTTTTGTTTTTGTTTTGAGACAGAGTCTCACTCCCTCACCCG

GGCTGGAGTGCAGTGGTGCGATGTTGGCTCACTACAACCTCATCCTCCCAGGTTCAAGCG

ATTCTCGTGCCTCAACCTCCTGAGTAGCTGAGACCACAGGCGTGCGGCTCCACACCTGGC

TAACTTTTTGTATTTTTAGTAGAGATAGGGTTTTGCCATGTTGGCCAGGCTGGTCTCAAA

CTCCTGACCTCAAGTAATGCGCCTGCCTCAGCCTCCCAAAGTGCTAGGATTACAGGGATG

AGCCACCATACCGGCCGCCACTCATCCTTCTTGATCATAATCCTCTCCCTCTATACATGC

AAGCTTTATCCTTTTAAGGAAATCAACTCCTTACATTTCTCTTTAGTTTATGACCTGTGT

ATCTCTCAACAATGCAGCTTAATTTTGCAGCTTTCAAACTTGATAGAACTGAAATTGTGC

AGTATGGATGCTATTGGGTCAGACTCTTTTCACACAATGTTATGTGAAGTTGTTGCACCT

TCTCTCATGGGCCTACTCCAGTTTGGCTTTCTCCACCCCACTGAAACCACGGATCTTCAC

ATTGCCAAGCCTGCTGAGCAGCTCTCTGTTCTCTCATTTGGCCTGTCAGCAACAGTTGAC

ACAGCTGATTCCTCCTTTCCTCTTCAAACACCTTCTTCATTTGACTTCTGGGACGCTCCC

TTGGTTTTCCTCCTTCTCACTGTCCTTTGCCCAACTAAATGCTGGCTTGTCCTAAGGCTC

AGTCCTTGACCTCCTCTTCTCCAACTATTTCCTTTCTCTCCTACATCTCATCCAATTCCA

TGGCTTTTTTTTTTTTTTTGACGAAGTCTTGCTCTGTCACCCAGGCTGGAGTGCAGT

GGTATGATCTTGGCTCACCGTAACCTCCGCCTCAGGATTCAAGCAATTCTCCTGCCTCA

CCCTCCTGAGTATCTGGGACTACAGGCACGCACCACCACACACGGCTAATTTTCTGTATT

TTTTGGTAGAGACAGGGTTTCACCATGTTGGCCAGGCTGGTCTCAAACTCCTGGCCTCAA

GTGATCCACCTGCCTCAGCCTCCCAAAGGGCTGGGATTATAGGCATGAGCCACTGTGCCC

AGCCTAATCCTGTGGCTTTAAATACCACTTATATCCATCAATGGTTCCCCAAATTTAAAT

CTTTCCCAAATTCAAATTTCCGTCCTCTTCTCTCCCCTAAGCTGCTGACTACTTACCCAC

TGCCTATTCAACATCTCCACTAGGGATATTTAAAAAGAATCTGAAATTTCATTTCTGATT
```

-continued

```
CCCCTCTCCTCCCCAAAGCCTTCAAATCTGCTTCTCCCCAGTCTTCCCATCTCAGTATT
TCCAGTTGCTCAAGACAAAAACCTGGAAGTCCTTCTTTATCCTCACTTTCCTTCACGTGC
CAACTGCAAGCCATCAGCGATCTCATTTTCTCTACCTTCAAAATATATCATGCTTCCGGC
CCTGTCTCACCACCTCCAGCTCCAGCATCCTACTCTAAGCAACTCTTATTTCTCTCCTAG
ATTACTGAAATAGCCTCAACTGCTCTCTCTGCTCCCTTTCTTGCCCACCCCCCATCATTT
ATTCTCTACTCAGGAGGTAAACTTATAAGAAACAAAATCAGATCCTATCATTCCCCTGTT
CAAAACCTACCCTTGGCTTCTCATGAGACTTGGAATAAAATCCAAATGGCTGTCACAGC
CTCAGGGCTCTACATGATGTGGGCCCTGGTGATCTTGCTGACCTCATCCCCAGTACTTTA
TCCTGGCTCCCATACTCCAATCCCCTGGGCACTCTTGCTGGTCCTAGAATCTCCAAGCCC
ATTCCCTCCTCAAGACCCTTTCCCCACAGTTCTGAATGGCTCACTTCATCTCATCATCCA
GTTCTCTCCTCAGGGAGGTTTTCCCTGAGCACCTCTCCTCTCAGTCACTCTCTATCCCCT
TTCATTGCTTTATTGCCTTCACTGCCCCTACATGATTTCGGATCACAAAATCTATTTACT
CACAAGAAAATAAGCTCCATGAATCTACAGACCTTTTTGCCATTTCCACAGCAGTATGTC
CCATCCCTAGAATATCTGGCACCTGGTTAAGTGTTCAGTACATATTTGTTGAATGGGTAA
ATGAATGAGAGCTGGAGGGAAATCCAAACTCAGGGGTGCCTGTGCCACAGCAAACACTCT
CCCTCTCACACCACCTGGAATAGAGATCAGCTAGAGCAGAGGCTGCTAAGAGAGGGAACA
GAGGCTCCTTGTGACAGGGAGACTAGGATCAGAAGTCAGGGAAGGGACAGCCGGGTGAAA
TGACTGGAAAGAGGAGCAATCACTCAGCAGTAAGGCAGGTTCTTCCAAAGACAAAAAGGA
CACAGAGATAAGTCAGGGCACTTCCAAGGAACCCAACTACCTACTCCACACTCCCAAATT
TATTCTGGGTTGGGCCCTTTTTGGTTCCAATATCACCTCGGATACCATAACTTGTCCAAG
GTCTCTTCTTACCTCTCCCACCCTAAATGAAGACGGGCCCTGGGTCCTAATCATACATTC
CTTTTTCCTCCACTGTGAGCTGAGACAAAGCCCTTAAGAGGAGATTCTCCTTGGCAACAA
ACTTAAAGGGTTAAAACCTAGAAGAATACTAATTCTTGCTGAGCTCCTACTATGATTTGA
TAATCACTGTACTACAGACTAATTACTACAATTCAAATGGTTTATATAAACCACTTAAAA
CAGTGCCTGTTACATAGTAAGCACCATATAAATACTGAGTTTTAACAATAATAATTGTTA
TTATTGTTATCACTATTTGTCAGGCATTCTTACACTCTCTTAACACTATTCCCATCATTC
CTCACATCCATTCTTTTTTTTTAAAGACAGGGTCTCTATCAGCCAGGCTGGAGTGCAGTG
GCACAATCATAGCTCACTGCAGCCTTGAACTCTTGGGCTCAAGTGATCCTCCTGCCTCAG
CCTCTGAAGTAGCAGAGACTACAGGCACATACCACCACACTTGGCTAGTTTTCTTTATCT
TTTGTAAAGATGGGGTTTCACTATGTTGCCCACACTAGTCTTGAGCTCCTGGTCTCAAGC
AATCCTCCCACCTCAGCCTCCCAAAGCGCTGGGACTATATAGGCATGAGCCCTCACACAT
GGCCGTCATCCATTCTTTTACTCAGGTATCAATGTCCTTATTTTAAAATCAAAGTAACT
AAGACTCAGAGTAGCAAAATCACTTACTCAAGACCTCACAGCTGAGAAGAGGTGGAATTT
AACTCAGGCTGTCATGATCCTTCCACTGCAGCAGACGCCTCTTCTGCCTTGCCCACCGCC
ACTGGCAGAGATCACCCCTCAGACACCCTGGGGCCTAATGAGACCTGATCGCCCTCTCTC
TTCTCCGAATATGAAAACTCTGTACCTCCTTGGAGGCCACCACGCACAAGCTGCCACTTC
CTTACCCACACAGCCGATGGTCACCACCCCATCCTTGTAGCGCTCTTGGGTTGGGCCAGT
TGGCTCCATTGCTGAATCAGTCTGCTGCTCCACCAGGACTGCTGGGCCATCCTCCTCTTC
CTCCTCCTCCCCAGAGCCATTACCCCAGGTGGCCCCAGCCACATCCCGAGCAATCTTCTC
CCGCCAGCTGCTCAAGTCCACTGCTCAAAGAAGGAGAAGATTAAAGAGGTTCTCCCCAGG
GCTGCTGTGCATGATGGCACATACTGTGCCCTGCACAGATTATGTAACTGGCACCCTCTG
```

```
GAGTTGTACAGTGCCAACCTAAATAAGAGCAGGTCAGAGAATCTCCCAAAAGTCATTTGA

CCCTACCCTCCCTGGAATCACGCACGTTTCTCTGAGCTTCTGAAAAGTACTGGGAAGGCT

AAAGGCAGCAAGCCACTGAGGCTCCTGACTACCTGCTGCCTCTCGTCCCACCAAGTCAGT

CTGCTCCTTATTCTGTCCCTTCCCCTGGCCTCTTGCACATATCCACCATAGAGGGGTTGG

CTTCAGGAAAGGTGAGCAAAATGATTCTGCATCTTTGGTCTCCCCCATGTCCTCCTACAG

CCCTCCTCTAAGGGCCACATACCTTTCCCCACAGTGATGGCTTCACAGGCTCTCAGCAAC

TGCTCTGGCCCCAGGGCCCGAGTCCATCCTCTCCCCCGCCTCCGACTCTTCTTCAAGACT

GAGATCAGAGGGCACAAAAGGATGGGCACACGGGCTTAGGCCTCTCATCTCTCCCACCAC

CCTTAGGCCCAAGACCAGGTGCCCCCTTGTCAATAAGCCTCTCTGTTCTCCCCTTTGTCC

CCTGCCAACTCACCTCTCCCAAGTTGCCCTCTCATTGCCCACTCACCACTACTAGGAT

CCTGTGGGTGCGGGGTCCCGAGGAAAGAGGTGAAAAGGACGACGTGGAGCTGGGGAT

AGTGTTGATGGAAATAATGCTTCCAGGCAACCACAAGAGCTGGCGGGGCCAGATCCACCT

TGTTCAAAACCAGCACCAGGGCCAGTCCAAGTTCTCCAGTCACATACTCATAAAGTGCTG

GCGGGAAATTCACAACCTAGGACAGAGTTGATAAGAGGATGGAGCAGTGAAAGTCAACCC

AGAGTTCTCTGCCTCCAGCTCCCCACTCAGCAGGTGTAGCTCAGAGACAAGGCCCTGGTG

GTAGCAGACTCTGGGCTAAAAACTATAAACCAGACAAACTGAAAAACAAAGACAAAACAG

GGGTTAGTAATACTTCTGAGTCTCAGAGGGCTTCCTATAGGTCATGATTAGAGATGGAAA

TGAACCCAAAACAAGACAAGGAAACAGCATCACTTAGCACACTGAGGTAAAGGCTGGGAT

CGGAAACAGGGATGGGGGTTAGGGTAGAAATTAGTCTGCTTTTTTGTGTGTGCACAACTA

TGTAAGTGTGTACACGTGCATATATGCATGCATGCAAGTACGTGCACATGTGTGCATGTT

TGTGTGTTAATGTGACTGTGAACATGTGTGCAAACATGCCTGTGTATATTGATGTGCACA

TGATGTACGTGTGAGTATGTGTGTACATATTATTAAGGACCTCCAACCTAAATGGTCC

TCACAGACCTCCCTTTCTCCCACTGGAGGACAAGAGTGAAGTTGCAGAGCTAGGATTCAC

ACAGGGCAGTCCAGCAGCAGTCTACAGCCTTAACTACTACTCTAGCATTCCAGGTGGGTT

CTGTAGCAACTGATGTGGCAGTGCTAGAGAAATGAGATAAGGAAGAAAGGGCATCTTTGG

GCTGGGCAGGAGGAAGTCCCCAGCTGCATTCATAGAATCCCTGGAGCTCCAACACTTGGA

TTTTCTATTGGTCTGTGATGAGCTAAAGGACAGGACATGGCTGTTTTGAAGAGAAGAGTG

AGCTGGCCAAGGGAGGAATGACAGGCTATAAGAGAATAAAAAACTGAGTTCCTAACTGCG

GACATCAGCACTAGGTAGAGATTAGAAAGACAGGAAGATAGATACCTCTCTGTCTCCCAA

CTCTTGCCTCTGACCTTTGCCCCTGAAAAACCTTTCTCCCTCCTCCTTGCCCACCCTTAT

CCCTAGTACTCACTGGATGTCGGATATCAGTGATAAGCAGGACGATGTCAGACATCTCTA

ACACCCGCCACAGCTGCCTCCATGTCTAAAAAGACAGGATCAGGAAGAGAAACTGAAAAC

AGAGTCCCTCTCCAGCCTGATCCCAAACCAATTTGACCATAGGTCACTATGCCCCACTCC

TGTCCCTAGAGTACACTGTCACCTCCAGATTGTGCTCAAAGTAGCTGAGTTTCTCAGAGG

AGTAAGCCCCATGAATCTTCCCAAGATAGTCTTGGAAGCTCCGTTCCTCTTGGCTCATTA

GTTGCTCCTTGGACATCTCATAGCTCCAAGGAGGACGTCGAGGAAAGTCCAGAACTGGGA

ATTCAGGAAAAAGTCCAAGTGTGAGGAAATCTTCAGGATTCAAGAGTACATCCCAGACCC
```

-continued

```
CTCCTTCCTCACAGTCGGCTTTTACCTTTCCAAACTCCTTCCCCAGCCCAATGCCTGTCT

TGCTCTCACTCACCTGAGCCAGGCTGATACACCTCCCGGATGTCCAGCTCCAACAACTCA

GCACTGACCGGCTGTAGAACTTGCTCCCGGGCTGCTCTCTTTCTCCTCTCTACCTCCTCC

CTGCTGTCTCTCTCAAAATGCAGTCGGTATCTAAGGGAACAGGGACCGAGACATCCAGAG

CAATCCTGTGGCCACAAACTCCTATTTTCTCCCCTCTTGTACAATCAACTTCGCAAACCA

TTCTCTCCAGAGTCGTTCAAGTCTCCTCTCTCAAGTCAGACTTCCCCCAAGTCCTTCTTT

CAGGCAATACTCAGCCTTCTCCTTCTAAAAGCCCAACTCTCTCCAGCCCCTCTGGAAAGG

AAGACTGTGGCCCGCTGTGGGGAGCCGAGTGGCTAGCGGAGAACTGTGGCATCCCAGGCC

CACCGTCTTCACCAGTAGCAGCCCGCTTTCCCCCAAAGCTCTGACTTCCGGGTAGGCGGG

AAAGCCGGGACCAGCGCCCCCTCCCACCCTCACCGATTTGGGTCGTAGCCTCGTGGACCC

AGCCCCTGAGAAGGCTGCTGGTTAAGCCTGCGGATATGATGGGTCACAGACTCCCCGTCC

GAGGTGTCGGTCTGTTCCTCTCGCCGCTCCCGGCTCCCGCTGCGGCTGTTGGAACTGGAG

CGCAGCCCATCTTGAAGCCCTGCGGGAGGGGCCGGTGACGCCAGTGCTGGCCAGCTCTC

AGGGGCCATAAGACCCTCTCCCCCATCGGCCTGACTCCCTTTCATCCCACTCAACTTCTT

CCGATGTTCAGTCCTCCCAGACACCCTATTTGGGACCCTCCCGGATGTGCGTGGGGGGAG

TCACTCCTTCAGGGAGCAGTGGGGACGGCGCCCCGTGCTAGCTGGAGGGATTCCCCTCCC

CCAACTCTCCATCCTTCCCCACCCCTTCCAGATGTAGGGGGGTGGGGGATCCCCTCCGC

GATAGGCCGCGAGGGTTGACGCGGTCCCACGACCCCTCCCACGATCCCAGAGGTGCAG

CGGGCACACCCCTCCTTCCAGATGTGCGGAAGCCCGAGCCCCGCCCCCTCCTCCCGCTCC

CGCACTGACCTCTCTTCCGCTCCCGTTTGTCCTGCAACTGCTTCTTCTTCTGCTTCACGC

TGAATGGCTTCTTCCTCGGCATGGCCCGGACCAGTCACCTGGCCCGCCCTCCGCCGAGCT

CCCGCCGCCTCAACTGACTGCCCCCCGGGGCAGCCCCCGCCGCAGGGGCCCGGGACCCTA

GAGGAGGCGGGGCTAGCAGGTGACGTCAGCGGGCGGGCCCGACAGAATTACCGCCGCGGC

GGCGATGGAAGGCGGACGGGGGAGATATAGTCACTTCCCTCCAGGA
```

Both PCR products were used to generate libraries of DNA fragments using the following protocol:

The DNA is first prepared for ligation to forked adapters by: fragmentation of the DNA by nebulisation, end repair of the DNA ends to make them blunt-ended and phosphorylation, then the addition of a single 'A' nucleotide onto the 3' ends of the human DNA fragments. The ligation reaction is performed with the prepared fragmented DNA and adapters pre-formed by annealing 'Oligo A' and 'Oligo B' (sequences given below). The product of the reaction is isolated/purified from unligated adapter by gel electrophoresis. Finally, the product of the ligation reaction is subjected to cycles of PCR to selectively amplify ligated product that contains adapter at both ends of the fragments.

Materials and Methods

Nebulization

Materials:

| | |
|---|---|
| Human RF I DNA (1 mg/ml) | NEB #N3021L |
| Buffer (glycerol 53.1 ml, water 42.1 ml, 1M TrisHCl pH 7.5 3.7 ml, 0.5M EDTA 1.1 ml) | |
| Nebulizer | Invitrogen (#K7025-05) |
| Qiagen columns | PCR purification kit (#28104) |

Mix: 25 µl (5 micrograms) of DNA
725 µl Buffer

```
Oligo A:
                                        (SEQ ID NO: 7)
5' ACACTCTTTCCCTACACGACGCTCTTCCGATC-x-T
(x = phosphorothioate bond)

Oligo B:
Phosphate-
                                        (SEQ ID NO: 8)
5' GATCGGAAGAGCTCGTATGCCGTCTTCTGCTTG
```

Procedure:

Chilled DNA solution was fragmented in the nebulizer on ice for 5 to 6 minutes under at least 32 psi of pressure. The recovered volume (usually somewhere between 400 and 600 µl) was split into 3 aliquots and purified with a Qiagen PCR-purification kit, but using only one column, and finally eluted in 30 µl of EB (Qiagen).

End-Repair
Materials:

| T4 DNA Polymerase | NEB #M0203S |
| 10x NEB 2 buffer | NEB #M7002S |
| 100x BSA | NEB #M9001S |
| dNTPs mix (10 mM each) | NEB #N0447S |
| E. coli DNA Pol I large fragment | (Klenow, NEB #M0210S) |
| T4 polynucleotide kinase | NEB #M0201S |
| T4 PNK buffer | NEB #M0201S |
| 100 mM ATP | |
| Qiagen columns | PCR purification kit (#28104) |

End repair mix was assembled as follows:

| DNA | 30 µl |
| Water | 12 µl |
| 10x NEB2 | 5 µl |
| 100x BSA | 0.5 µl |
| 10 mM dNTPs | 2 µl |
| T4 DNA pol (3 U/µl) | 5 µl |
| | 50 µl total |

The reaction was incubated for 15 min at room temperature, then 1 µl of E. coli DNA Pol I large fragment (Klenow) was added and the reaction incubated for a further 15 min at room temperature. The DNA was purified from enzymes, buffer, etc by loading the reaction mix on a Qiagen column, and finally eluting in 30 µl EB. The 5′ ends of the DNA were then phosphorylated using polynucleotide kinase as follows:

| DNA | 30 µl |
| Water | 9.5 µl |
| 10x PNK buffer | 5 µl |
| 100 mM ATP | 0.5 µl |
| T4 PNK (10 U/µl) | 5 µl |
| | 50 µl total |

The reaction was incubated for 30 min at 37° C., then heat inactivated at 65° C. for 20 min. DNA was then purified from enzymes, buffer, etc by loading the reaction mix on a Qiagen column, finally eluting in 30 µl EB. Three separate tubes were pooled to give 90 µl total.

A-Tailing Reaction
Materials:

| Taq DNA polymerase | NEB #M0267L |
| 10x thermopol buffer | NEB #B9004S |
| 1 mM dATP | Amersham-Pharmacia #272050 |
| Qiagen MinElute column | PCR purification kit (#28004) |

The following reaction mix was assembled:

| DNA | 30 µl |
| 10x thermopol buffer | 5 µl |
| 1 mM dATP | 10 µl |
| Taq pol (5 U/µl) | 3 µl |
| | ~50 µl total |

The reaction was incubated for 30 min at 70° C., then the DNA purified from enzymes, buffer, etc by loading the reaction mix on a Qiagen MinElute column, and finally eluting in 10 µl EB.

Anneal Forked Adapter
Materials:

| 'Oligo A' and 'Oligo B' | |
| 50 mM Tris/50 mM NaCl pH 7 | |
| PCR machine | |
| 100 µM Oligo A | 20 µl |
| 100 µm Oligo B | 20 µl |
| Tris/NaCl | 10 µl |
| | 50 µl at 40 µM duplex in 10 mM Tris/10 mM NaCl pH 7.5 |

The adapter strands were annealed in a PCR machine programmed as follows:
Ramp at 0.5° C./sec to 97.5° C.
Hold at 97.5° C. for 150 sec
Then a step of 97.5° C. for 2 sec with a temperature drop of 0.1° C./cycle for 775 cycles Ligation Reaction
Materials:

| 15 µM forked adapter | |
| A-tailed genomic DNA | |
| Quick Ligase | NEB #M2200L |
| Quick Ligase 2x buffer | NEB #M2200L |
| PCR machine | |
| Qiagen columns | PCR purification kit (#28104) |

Reaction mix was assembled as follows:

| DNA | 10 µl |
| 2x buffer | 25 µl |
| 40 µM adapter | 10 µl |
| Quick Ligase | 5 µl |
| | ~50 µl total |

The reaction was incubated for 20 min at room temperature then the DNA purified from enzymes, buffer, etc by loading the reaction mix on a Qiagen column, and finally eluting in 30 µl EB.

Gel Purification
Materials:

| Agarose | Biorad #161-3101 |
| 100 base pair ladder | NEB #N3231L |
| TAE | |
| Loading buffer (50 mM Tris pH 8, 40 mM EDTA, 40% w/v sucrose) | |
| Ethidium bromide | |
| Gel trays and tank. Electrophoresis unit | |

The entire sample from the purified ligation reaction was loaded into one lane of a 2% agarose gel containing ethidium bromide and run at 120V for 50 min. The gel was then viewed on a 'White-light' box and fragments from above 300 bp to at least 750 bp excised and purified with a Qiagen Gel purification kit, eluting in 30 µl EB. For large gel slices two minElute columns were used, eluting each in 15 µl EB and subsequently pooling the two eluates.

PCR Amplification
Materials:

```
Ligated DNA
PRIMER 1:
                                       (SEQ ID NO: 9)
AATGATACGGCGACCACCGAGATCTACACTCTTTCCCTACACGA PRIMER 2:
                                       (SEQ ID NO: 10)
CAAGCAGAAGACGGCATACGA Sigma (#P0982)
2x Jump Start RedTaq PCR mix
PCR machine
Qiagen(#28004)
Qiagen MinElute columns
```

The purified ligated DNA was diluted 25 fold, then a PCR reaction mix prepared as follows:

| | |
|---|---|
| DNA | 1 μl |
| 2x Hot Start Red Taq mix | 25 μl |
| 100 μM P5 | 0.5 μl |
| 100 μM P7 | 0.5 μl |
| Water | 23 μl |
| | ~50 μl total |

```
Primer P5:
                                      (SEQ ID NO: 11)
5'-AATGATACGGCGACCACCGAGAAAAACGCCAGCAA Primer P7:
                                      (SEQ ID NO: 12)
5'-CAAGCAGAAGACGGCATACGATCCGACAGCTT
```

Thermocycling was carried out in a PCR machine under the following conditions:

| |
|---|
| 2 min @ 94° C. |
| [45 sec@ 94° C., 45 sec @ 65° C., 2 min @ 70° C.] 16 cycles |
| 5 min @ 70° C. |
| Hold @ 4° C. |

PCR products were purified from enzymes, buffer, etc on a Qiagen MinElute column, eluting in 10 μl EB. The resulting DNA 5' and 3' modified library is ready for amplification on a surface PCR platform.

Validation of 5' and 3' Modified Library

1 μl of the DNA 5' and 3' modified library was cloned into a plasmid vector and plated out on agar. Colonies were picked, miniprepped and the cloned inserts sequenced by conventional Sanger sequencing. The sequence data of the genomic inserts (excluding vector and adaptor sequences) obtained including the position of the insert in the PCR product was as follows:

Primer Set 1 PCR Product 5' and 3' Modified Library:

```
Clone 1 Position in PCR product = 7105-7413
                                                 (SEQ ID NO: 13)
CTCTTCTTCAAGACTGAGATCAGAGGGCACAAAAGGATGGGCACACGGGCTTAGGCCTCT

CATCTCTCCCACCACCCTTAGGCCCAAGACCAGGTGCCCCCTTGTCAATAAGCCTCTCTG

TTCTCCCCTTTGTCCCCTGCCAACTCACCTCTCCCAAGTTGCCCTCTCTCATTGCCCACT

CACCACTACTAGGATCCTGTGGGGTGCGGGGGTCCCGAGGAAAAGAGGTGAAAAGGACGA

CGTGGAGCTGGGGATAGTGTTGATGGAAATAATGCTTCCAGGCAACCACAAGAGCTGGCG

GGGCCAGAT

Clone 2 Position in PCR product = 5535-5773
                                                 (SEQ ID NO: 14)
TGTAAGAATGCCTGACAAATAGTGATAACAATAATAACAATTATTATTGTTAAAACTCAG

TATTTATATGGTGCTTACTATGTAACAGGCACTGTTTTAAGTGGTTTATATAAACCATTT

GAATTGTAGTAATTAGTCTGTAGTACAGTGATTATCAAATCATAGTAGGAGCTCAGCAAG

AATTAGTATTCTTCTAGGTTTTAACCCTTTAAGTTTGTTGCCAAGGAGAATCTCCTCTT

Clone 3 Position in PCR product = 5601-6103
                                                 (SEQ ID NO: 15)
GGCCATGTGTGAGGGCTCATGCCTATATAGTCCCAGCGCTTTGGGAGGCTGAGGTGGGAG

GATTGCTTGAGACCAGGAGCTCAAGCTAGTGTGGGCAACATAGTGAAACCCCATCTTTA

CAAGAGATAAAGAAAACTAGCCAAGTGTGGTGGTATGTGCCTGTAGTCTCTGCTACTTCA

GAGGCTGAGGCAGGAGGATCACTTGAGCCCAAGAGTTCAAGGCTGCAGTGAGCTATGATT

GTGCCACTGCACTCCAGCCTGGCTGATAGAGACCCTGTCTTTAAAAAAAAGAATGGATG

TGAGGAATGATGGGAATAGTGTTAAGAGAGTGTAAGAATGCCTGACAAATAGTGATAACA

ATAATAACAATTATTATTGTTAAAACTCAGTATTTATATGGTGCTTACTATGTAACAGGC

ACTGTTTTAAGTGGTTTATATAAACCATTTGAATTGTAGTAATTAGTCTGTAGTACAGTG

ATTATCAAATCATAGTAGGAGCT
```

Clone 4 Position in PCR product = 636-1041

(SEQ ID NO: 16)
CCATGTGCCTGGCTTCGCCCCACCTGGTTTCAGCTGCTCTTCCTTACCTGCCTCGCCTTT

TACCCTTCCCTGTCTCCTTTCCTCTCCTCAGAGATTCTGCCATTGATGAAGCTGCTGTCC

ACTCACCCCTAGATTTTTGTTGCATAGCAGTAAGATCTCTGGCCTGGAATGTTTTGGGGA

AAACTGGAAGGACTGTGTTATGGGAGTGGGAGTATAACTGGTACCTGGTTAATGCTTTCC

CTTTCCATTATTCTTTTCTTCCTCCAGCCTGGGCAGAGAAACGTGGTTACAAGACAGCCA

AGGCGGCTCGGAATGATGTGTACAGAGCAGCCAACAGTCTCTTGCGGCTGGCAGTGGACG

GCCGCCTCAGCCTGTGTTTTCATCCCCCAGGCTACAGTGAACAGA

Clone 5 Position in PCR product = 2-298

(SEQ ID NO: 17)
GAGGAACTCAGCACTCATCCTCACCCAGCAGGGCATAAGGGTTTCGGCCAGCCAGGCTGG

ACCCTGGAGCCGAGGTTGGGGTCTCCTCATCCCCTTCTCCCTCCTCATCCGCATCCCGGT

CCTCCTCTCCCTCCTCCCCACAGGAGCTGCTCAGCTCTTCCTCTTCCTCCTCCTCCTCGT

CACCTGCTGGCCCCACCCTGCCCTGCAAAACCACCAGCTCCGTGGTCTCTGGATGGGACT

CCCAGGTGCCTGGGGAACCAAAACAAGAAAAAAATGGAGGAGAGTTTTGAGCAAGAA

Clone 6 Position in PCR product = 1-411

(SEQ ID NO: 18)
CGAGGAACTCAGCACTCATCCTCACCCAGCAGGGCATAAGGGTTTCGGCCAGCCAGGCTG

GACCCTGGAGCCGAGGTTGGGGTCTCCTCATCCCCTTCTCCCTCCTCATCCGCATCCCGG

TCCTCCTCTCCCTCCTCCTCACAGGAGCTGCTCAGCTCTTCCTCTTCCTCCTCCTCCTCG

TCACCTGCTGGCCCCACCCTGCCCTGCAAAACCACCAGCTCCGTGGTCTCTGGATGGGAC

TCCCAGGTGCCTGGGGAACCAAAACAAGAAAAAAATGGAGGAGAGTTTTGAGCAAGAACT

AAAGCCAAGGAAAGATGGGGAAGAGGCAAAGACTAGGAATAACAATAATCTTTAGAGCTG

CTGGCATTCATTCATTCATCCATTCATTCAACTTCCTATGTGCAGATTGCT

Clone 7 Position in PCR product = 3059-3448

(SEQ ID NO: 19)
CTGAGTAGCTGAGACCACAGGCGTGCGGCTCCACACCTGGCTAACTTTTTGTATTTTTAG

TAGAGATAGGGTTTTGCCATGTTGGCCAGGCTGGTCTCAAACTCCTGACCTCAAGTAATG

CGCCTGCCTCAGCCTCCCAAAGTGCTAGGATTACAGGGATGAGCCACCATACCGGCCGCC

ACTCATCCTTCTTGATCATAATCCTCTCCCTCTATACATGCAAGCTTTATCCTTTTAAGG

AAATCAACTCCTTACATTTCTCTTTAGTTTATGACCTGTGTATCTCTCAACAATGCAGCT

TAATTTTGCAGCTTTCAAACTTGATAGAACTGAAATTGTGCAGTATGGATGCTATTGGGT

CAGACTCTTTTCACACAATGTTATGTGAAG

Clone 8 Position in PCR product = 3492-3772

(SEQ ID NO: 20)
TAAAAAAAAAGCCATGGAATTGGATGAGATGTAGGAGAGAAAGGAAATAGTTGGAGAAGA

GGAGGTCAAGGACTGAGCCTTAGGACAAGCCAGCATTTAGTTGGGCAAAGGACAGTGAGA

AGGAGGAAAACCAAGGGAGCGTCCCAGAAGTCAAATGAAGAAGGTGTTTGAAGAGGAAAG

GAGGAATCAGCTGTGTCAACTGTTGCTGACAGGCCAAATGAGAGAACAGAGAGCTGCTCA

GCAGGCTTGGCAATGTGAAGATCCGTGGTTTCAGTGGGGTGG

Clone 9 Position in PCR product = 1-503

(SEQ ID NO: 21)
CGAGGAACTCAGCACTCATCCTCACCCAGCAGGGCATAAGGGTTTCGGCCAGCCAGGCTG

GACCCTGGAGCCGAGGTTGGGGTCTCCTCATCCCCTTCTCCCTCCTCATCCGCATCCCGG

TCCTCCTCTCCCTCCTCCTCACAGGAGCTGCTCAGCTCTTCCTCTTCCTCCTCCTCCTCG

TCACCTGCTGGCCCCACCCTGCCCTGCAAAACCACCAGCTCCGTGGTCTCTGGATGGGAC

-continued

TCCCAGGTGCCTGGGGAACCAAAACAAGAAAAAAATGGAGGAGAGTTTTGAGCAAGAACT

AAAGCCAAGGAAAGATGGGGAAGAGGCAAAGACTAGGAATAACAATAATCTTTAGAGCTG

CTGGCATTCATTCATTCATCCATTCATTCAACTTCCTATGTGCAGATTGCTGAACAGAAC

CTTTGTGCGCATCAACTTCAATCTTTACAATCACTATGCTAAGGGTCAATTATTACCCTC

AGTTTGCAGATCAGGAAAATATC

Clone 10 Position in PCR product = 5567-5860

(SEQ ID NO: 22)
CACTGCACTCCAGCCTGGCTGATAGAGACCCTGTCTTTAAAAAAAAAGAATGGATGTGAG

GAATGATGGGAATAGTGTTAAGAGAGTGTAAGAATGCCTGACAAATAGTGATAACAATAA

TAACAATTATTATTGTTAAAACTCAGTATTTATATGGTGCTTACTATGTAACAGGCACTG

TTTTAAGTGGTTTATATAAACCATTTGAATTGTAGTAATTAGTCTGTAGTACAGTGATTA

TCAAATCATAGTAGGAGCTCAGCAAGAATTAGTATTCTTCTAGGTTTTAACCC

Clone 11 Position in PCR product = 9224-9455

(SEQ ID NO: 23)
CCTACCCGGAAGTCAGAGCTTTGGGGGAAAGCGGGCTGCTACTGGTGAAGACGGTGGGCC

TGGGATGCCACAGTTCTCCGCTAGCCACTCGGCTCCCCACAGCGGGCCGCAGTCTTCCTT

TCCAGAGGGGCTGGAGAGAGTTGGGCTTTTAGAAGGAGAAGGCTGAGTATTGCCTGAAAG

AAGGACTTGGGGGAAGTCTGACTTGAGAGAGGAGACTTGAACGACTCTGGAG

Clone 12 Position in PCR product = 5836-6150

(SEQ ID NO: 24)
TATCAGCCAGGCTGGAGTGCAGTGGCACAATCATAGCTCACTGCAGCCTTGAACTCTTGG

GCTCAAGTGATCCTCCTGCCTCAGCCTCTGAAGTAGCAGAGACTACAGGCACATACCACC

ACACTTGGCTAGTTTTCTTTATCTTTTGTAAAGATGGGGTTTCACTATGTTGCCCACACT

AGTCTTGAGCTCCTGGTCTCAAGCAATCCTCCCACCTCAGCCTCCCAAAGCGCTGGGACT

ATATAGGCATGAGCCCTCACACATGGCCGTCATCCATTCTTTTACTCAGGTATCAATGTC

CTTATTTTTAAAATC

Clone 13 Position in PCR product = 5783-6198

(SEQ ID NO: 25)
GTGAGGTCTTGAGTAAGTGATTTTGCTACTCTGAGTCTTAGTTACTTTGATTTTAAAAAT

AAGGACATTGATACCTGAGTAAAAGAATGGATGACGGCCATGTGTGAGGGCTCATGCCTA

TATAGTCCCAGCGCTTTGGGAGGCTGAGGTGGGAGGATTGCTTGAGACCAGGAGCTCAAG

ACTAGTGTGGGCAACATAGTGAAACCCCATCTTTACAAAAGATAAAGAAAACTAGCCAAG

TGTGGTGGTATGTGCCTGTAGTCTCTGCTACTTCAGAGGCTGAGGCAGGAGGATCACTTG

AGCCCAAGAGTTCAAGGCTGCAGTG

Clone 14 Position in PCR product = 5836-6150

(SEQ ID NO: 26)
TATCAGCCAGGCTGGAGTGCAGTGGCACAATCATAGCTCACTGCAGCCTTGAACTCTTGG

GCTCAAGTGATCCTCCTGCCTCAGCCTCTGAAGTAGCAGAGACTACAGGCACATACCACC

ACACTTGGCTAGTTTTCTTTATCTTTTGTAAAGATGGGGTTTCACTATGTTGCCCACACT

AGTCTTGAGCTCCTGGTCTCAAGCAATCCTCCCACCTCAGCCTCCCAAAGCGCTGGGACT

ATATAGGCATGAGCCCTCACACATGGCCGTCATCCATTCTTTTACTCAGGTATCAATGTC

CTTATTTTTAAAATC

Clone 15 Position in PCR product = 1-283

(SEQ ID NO: 27)
CGAGGAACTCAGCACTCATCCTCACCCAGCAGGGCATAAGGGTTTCGGCCAGCCAGGCTG

GACCCTGGAGCCGAGGTTGGGGTCTCCTCATCCCCTTCTCCCTCCTCATCCGCATCCCGG

-continued

```
TCCTCCTCTCCCTCCTCCTCACAGGAGCTGCTCAGCTCTTCCTCTTCCTCCTCCTCCTCG

TCACCTGCTGGCCCACCCTGCCCTGCAAAACCACCAGCTCCGTGGTCTCTGGATGGGAC

TCCCAGGTGCCTGGGGAACCAAAACAAGAAAAAAATGGAGGAGAGTTTTGAGCAAGAACT

AAAGCCAAGGAAAGATGGGGAAGAGGCAAAGACTAGGAATAACAATAATCTTTAGAGCTG

CTGGCATTCATTCATTCATCCATT

Clone 16 Position in PCR product = 1-307
                                                        (SEQ ID NO: 28)
CGAGGAACTCAGCACTCATCCTCACCCAGCAGGGCATAAGGGTTTCGGCCAGCCAGGCTG

GACCCTGGAGCCGAGGTTGGGGTCTCCTCATCCCCTTCTCCCTCCTCATCCGCATCCCGG

TCCTCCTCTCCCTCCTCCTCACAGGAGCTGCTCAGCTCTTCCTCTTCCTCCTCCTCCTCG

TCACCTGCTGGCCCACCCTGCCCTGCAAAACCACCAGCTCCGTGGTCTCTGGATGGGAC

TCCCAGGTGCCTGGGGAACCAAAACAAGAAAAAAATGGAGGAGAGTTTTGAGCAAGAACT

AAAGCC

Clone 17 Position in PCR product = 1230-1484
                                                        (SEQ ID NO: 29)
CAGTACTTTCCTCAATGTCCCACCTTCTCTCTTTCCCTTACCCACCCTCCCCGTCATACC

TGCAACTGCCTAGGCAGAAGAGATGGGAAGATGAGGCCTGGGCAGTCACAGAGCTTCACA

GAGGGGGTAAGAAAGTAGGTCTGAAAGTATCGGGTATGGCCCGGGGTTCTGGAGACACTC

ACGACTTTCCGCCCCACCAGCCCATTGATCAGCGAGGACTTTCCCACATTAGGGAAACCT

GAGGAAGGCAAGGAA
```

Primer Set 2 PCR Product 5' and 3' Modified Library:

```
Clone 1
Position in PCR product = 2077-2246
                                                        (SEQ ID NO: 30)
AACCCCATCTCTACTAAAAATACAAAAATTAGCTGGGCGTGGTGGTGGGCGCCTGTAATT

GCAGCTACTTGGGAGGCTGAGGCAGGAGAACCACTTGAACCCAGGAGGCGGAGGTTGCAG

TGAGCTGAGATTGCACCATTGCACTCCAGCCTGGGCAATAAGAGGGAAAC

Clone 2
Position in PCR product = 8519-8740
                                                        (SEQ ID NO: 31)
CGGACATCAGCACTAGGTAGAGATTAGAAAGACAGGAAGATAGATACCTCTCTGTCTCCC

AACTCTTGCCTCTGACCTTTGCCCCTGAAAAACCTTTCTCCCTCCTCCTTGCCCACCCTT

ATCCCTAGTACTCACTGGATGTCGGATATCAGTGATAAGCAGGACGATGTCAGACATCTC

TAACACCCGCCACAGCTGCCTCCATGTCTAAAAAGACAGGAT

Clone 3
Position in PCR product = 10096-10485
                                                        (SEQ ID NO: 32)
TTGACGCGGTCCCACGACCCCCTCCCACGATCCCCAGAGGTGCAGCGGGCACACCCCTCC

TTCCAGATGTGCGGAAGCCCGAGCCCCGCCCCCTCCTCCCCGCTCCCGCACTGACCTCTCT

TCCGCTCCCGTTTGTCCTGCAACTGCTTCTTCTTCTGCTTCACGCTGAATGGCTTCTTCC

TCGGCATGGCCCGGACCAGTCACCTGGCCCGCCCTCCGCCGAGCTCCCGCCGCCTCAACT

GACTGCCCCCGGGGCAGCCCCCGCCGCAGGGGCCCGGGACCCTAGAGGAGGCGGGGCTA

GCAGGTGACGTCAGCGGGCGGGCCCGACAGAATTACCGCCGCGGCGGCGATGGAAGGCGG

ACGGGGGAGATATAGTCACTTCCCTCCAGG
```

-continued

Clone 4
Position in PCR product = 1296-1531
(SEQ ID NO: 33)
GCCCACAGCAGTGTAGGGCTCCTGGATCTGGGCGATAGGGTAGATCCCCGCCAGAACCTG

AGGGAAATGAGCACTCAGTACTTTCCTCAATGTCCCACCTTCTCTCTTTCCCTTACCCAC

CCTCCCCGTCATACCTGCAACTGCCTAGGCAGAAGAGATGGGAAGATGAGGCCTGGGCAG

TCACAGAGCTTCACAGAGGGGGTAAGAAAGTAGGTCTGAAAGTATCGGGTATGGCC

Clone 5
Position in PCR product = 6677-6969
(SEQ ID NO: 34)
GCTGCCTTTAGCCTTCCCAGTACTTTTCAGAAGCTCAGAGAAACGTGCGTGATTCCAGGG

AGGGTAGGGTCAAATGACTTTTGGGAGATTCTCTGACCTGCTCTTATTTAGGTTGGCACT

GTACAACTCCAGAGGGTGCCAGTTACATAATCTGTGCAGGGCACAGTATGTGCCATCATG

CACAGCAGCCCTGGGGAGAACCTCTTTAATCTTCTCCTTCTTTGAGCAGTGGACTTGAGC

AGCTGGCGGAGAAGATTGCTCGGGATGTGGCTGGGGCCACCTGGGGTAATGG

Clone 6
Position in PCR product = 6349-6508
(SEQ ID NO: 35)
GAGGTGGAATTTAACTCAGGCTGTCATGATCCTTCCACTGCAGCAGACGCCTCTTCTGCC

TTGCCCACCGCCACTGGCAGAGATCACCCCTCAGACACCCTGGGGCCTAATGAGACCTGA

TCGCCCTCTCTCTTCTCCGAATATGAAAACTCTGTACCTC

Clone 7
Position in PCR product = 6623-6815
(SEQ ID NO: 36)
TGCTGCTCCACCAGGACTGCTGGGCCATCCTCCTCCTCCTCCTCCTCCCCAGAGCCATTA

CCCCAGGTGGCCCCAGCCACATCCCGAGCAATCTTCTCCCGCCAGCTGCTCAAGTCCACT

GCTCAAAGAAGGAGAAGATTAAAGAGGTTCTCCCCAGGGCTGCTGTGCATGATGGCACAT

ACTGTGCCCTGCA

Clone 8
Position in PCR product = 4787-4973
(SEQ ID NO: 37)
ATGGCTGTCACAGCCTCAGGGCTCTACATGATGTGGGCCCTGGTGATCTTGCTGACCTCA

TCCCCAGTACTTTATCCTGGCTCCCATACTCCAATCCCCTGGGCACTCTTGCTGGTCCTA

GAATCTCCAAGCCCATTCCCTCCTCAAGACCCTTTCCCCACAGTTCTGAATGGCTCACTT

CATCTCA

Clone 9
Position in PCR product = 2868-3055
(SEQ ID NO: 38)
CTTTGACGACCACCACCAGACCTAGTTCTCTGTCCGCTTTGCAGGAAAACTCCTTAAAAG

ACTTACCTACTTTTTTCACCATTTCTTCCTGCTATCTTCTTTGTAACTGTAAACTACAAC

ATACAAAAAAATGCACAGAACATACATGTGCAGCCTGATGAACCCCATACCACCCAATGT

GTGACAAC

All of the sequences align to the PCR products used to generate the libraries. In the case of the 5' and 3' modified library made from 'primer set 1' four out of 17 of the sequenced clones have inserts that align to the ends of the original PCR product indicating an overabundance of end-sequences in the 5' and 3' modified library prepared from a PCR product generated with 5'OH unmodified primers. In contrast, zero out of nine of the sequenced clones derived from the 5' and 3' modified library made using 'primer set 2' have inserts that align to the ends of the original PCR product, indicating that the use of 5'-modified primers to generate the PCR product essentially eliminates the overabundance of the end-sequences from the 5' and 3' modified library.

The invention claimed is:

1. A method of reducing representation of the ends of a primary polynucleotide sequence in a library of fragments generated from said primary polynucleotide sequence, the method comprising:
   a) performing an amplification reaction with one or more modified amplification primers, said modified amplification primers comprising a modification configured to prevent fragments originating from the ends of the primary polynucleotide from ligating to an adapter, thereby forming a modified primary polynucleotide sequence;
   b) fragmenting the modified primary polynucleotide sequence such that the 5' terminal fragment and the 3' terminal fragment each comprise the modification and the internal fragments do not comprise the modification;
   c) ligating an adapter to the internal fragments generated in step b), thereby forming a library of ligated internal fragments generated from said primary polynucleotide sequence; and
   d) optionally purifying the ligated internal fragments by removing the unligated terminal fragments.

2. The method of claim 1, wherein said modified amplification primers comprise a 5'-amino or 5'-biotin modification.

3. The method of claim 1, wherein said modified amplification primers comprise a modification that prevents nucleotide polymerase mediated copying of the full length of the primer.

4. The method of claim 3, wherein said modified amplification primers comprise an abasic site.

5. The method of claim 1, further comprising e) amplifying the ligated internal fragments generated in step c).

6. The method of claim 1, wherein the fragmenting of step (b) is done by sonication or nebulization.

7. The method of claim 1, wherein the primary polynucleotide sequence is a DNA molecule.

8. The method of claim 7, wherein the modified primary polynucleotide is generated by polymerase chain reaction.

9. The method of claim 8, wherein the modified primary polynucleotide is at least 5000 base pairs in length.

10. The method of claim 1, wherein the primary polynucleotide sequence is a genomic DNA fragment.

11. The method of claim 1, further comprising end-repairing and phosphorylating fragments generated in step b).

12. The method of claim 11, wherein the end-repairing and phosphorylating comprises treating the fragments generated in step b) with a polymerase and a polynucleotide kinase.

13. The method of claim 1, wherein the purifying comprises selectively capturing the ligated internal fragments.

* * * * *